(12) United States Patent
Venkatasanthanam et al.

(10) Patent No.: US 11,471,253 B2
(45) Date of Patent: *Oct. 18, 2022

(54) DURABLE ORNAMENTAL INDICIA CARRIER

(71) Applicant: ALIGN TECHNOLOGY, INC., San Jose, CA (US)

(72) Inventors: Sriram Venkatasanthanam, Chino Hills, CA (US); Ramin Heydarpour, Beverly Hills, CA (US); John Y. Morton, San Jose, CA (US); Jun Sato, San Jose, CA (US); Michael Christopher Cole, Longmont, CO (US); Mehdi Mojdeh, Fremont, CA (US); Prashanth Vanchy, Los Angeles, CA (US); Natalia Lysaya Powers, San Jose, CA (US); Sibel Narin, Los Gatos, CA (US); Jeremy Riley, Mountain View, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 157 days.

This patent is subject to a terminal disclaimer.

(21) Appl. No.: 17/008,295

(22) Filed: Aug. 31, 2020

(65) Prior Publication Data

US 2021/0078357 A1     Mar. 18, 2021

Related U.S. Application Data

(60) Provisional application No. 62/901,091, filed on Sep. 16, 2019.

(51) Int. Cl.
*B32B 7/12* (2006.01)
*A61C 7/08* (2006.01)
(Continued)

(52) U.S. Cl.
CPC ............ *A61C 7/08* (2013.01); *A61C 13/0006* (2013.01); *B32B 7/06* (2013.01); *B32B 7/12* (2013.01);
(Continued)

(58) Field of Classification Search
CPC ....... B32B 7/12; B32B 27/20; B32B 2255/26; B32B 2307/408; B32B 2307/416
See application file for complete search history.

(56) References Cited

U.S. PATENT DOCUMENTS 3,089,487 A    5/1963    Enicks et al.
5,645,420 A    7/1997    Bergersen
(Continued)

FOREIGN PATENT DOCUMENTS

EP    2798973 A1    11/2014
EP    3275334 A1    1/2018
(Continued)

OTHER PUBLICATIONS

White J., "Decals Amp up the Fun of Wearing Invisalign," retrieved on Sep. 28, 2020 from https://smilesbywhite.com/blog/2018/decals-amp-up-the-fun-of-wearing-invisalign.

*Primary Examiner* — Elizabeth E Mulvaney
(74) *Attorney, Agent, or Firm* — FisherBroyles, LLP

(57) ABSTRACT

The present disclosure relates to ornamental indicia carrier and method of producing the same. In some embodiments, the ornamental indicia carrier comprises an ultraviolet light ("UV") cured ink printed on a thin flexible film and combined with an adhesive layer. The ornamental indicia carrier is capable of enduring the conditions inside the mouth for an extended period of time and can be used in conjunction with a dental appliance.

19 Claims, 18 Drawing Sheets

(51) Int. Cl.

| | | |
|---|---|---|
| *A61C 13/00* | (2006.01) | |
| *B32B 7/06* | (2019.01) | |
| *B32B 27/20* | (2006.01) | |
| *B32B 38/00* | (2006.01) | |
| *B41M 5/00* | (2006.01) | |
| *B44C 3/02* | (2006.01) | |
| *C09D 11/101* | (2014.01) | |

(52) U.S. Cl.
CPC ............ *B32B 27/20* (2013.01); *B32B 38/145* (2013.01); *B41M 5/0064* (2013.01); *B41M 5/0088* (2013.01); *B44C 3/025* (2013.01); *C09D 11/101* (2013.01); *A61C 2201/002* (2013.01); *B32B 2255/26* (2013.01); *B32B 2307/408* (2013.01); *B32B 2307/416* (2013.01); *B32B 2307/514* (2013.01); *B32B 2451/00* (2013.01); *B41M 2205/38* (2013.01); *B41M 2205/40* (2013.01)

(56) References Cited

U.S. PATENT DOCUMENTS

| | | |
|---|---|---|
| 5,820,368 A | 10/1998 | Wolk |
| 5,842,860 A | 12/1998 | Funt |
| 5,916,653 A | 6/1999 | Kunstadter et al. |
| 6,143,330 A | 11/2000 | Aaltonen et al. |
| 6,183,248 B1 | 2/2001 | Chishti et al. |
| 6,293,790 B1 | 9/2001 | Hilliard |
| 6,309,215 B1 | 10/2001 | Phan et al. |
| 6,386,864 B1 | 5/2002 | Kuo |
| 6,454,565 B2 | 9/2002 | Phan et al. |
| 6,471,511 B1 | 10/2002 | Chishti et al. |
| 6,524,101 B1 | 2/2003 | Phan et al. |
| 6,541,098 B2 | 4/2003 | Venkatasanthanam et al. |
| 6,572,372 B1 | 6/2003 | Phan et al. |
| 6,599,559 B1 | 7/2003 | Mcgee et al. |
| 6,607,382 B1 | 8/2003 | Kuo et al. |
| 6,705,863 B2 | 3/2004 | Phan et al. |
| 6,783,604 B2 | 8/2004 | Tricca |
| 6,790,035 B2 | 9/2004 | Tricca et al. |
| 6,814,574 B2 | 11/2004 | Abolfathi et al. |
| 6,830,450 B2 | 12/2004 | Knopp et al. |
| 6,867,254 B2 | 3/2005 | Wiercinski et al. |
| 6,905,337 B1 | 6/2005 | Sachdeva |
| 6,947,038 B1 | 9/2005 | Anh et al. |
| 7,074,039 B2 | 7/2006 | Kopelman et al. |
| 7,104,792 B2 | 9/2006 | Taub et al. |
| 7,121,825 B2 | 10/2006 | Chishti et al. |
| 7,160,107 B2 | 1/2007 | Kopelman et al. |
| 7,192,273 B2 | 3/2007 | McSurdy, Jr. |
| 7,199,180 B1 | 4/2007 | Simmons et al. |
| 7,204,691 B2 | 4/2007 | Darling et al. |
| 7,347,688 B2 | 3/2008 | Kopelman et al. |
| 7,354,270 B2 | 4/2008 | Abolfathi et al. |
| 7,448,514 B2 | 11/2008 | Wen |
| 7,481,121 B1 | 1/2009 | Cao |
| 7,543,511 B2 | 6/2009 | Kimura et al. |
| 7,553,157 B2 | 6/2009 | Abolfathi et al. |
| 7,600,999 B2 | 10/2009 | Knopp |
| 7,658,610 B2 | 2/2010 | Knopp |
| 7,766,658 B2 | 8/2010 | Tricca et al. |
| 7,771,195 B2 | 8/2010 | Knopp et al. |
| 7,854,609 B2 | 12/2010 | Chen et al. |
| 7,871,269 B2 | 1/2011 | Wu et al. |
| 7,878,801 B2 | 2/2011 | Abolfathi et al. |
| 7,878,805 B2 | 2/2011 | Moss et al. |
| 7,883,334 B2 | 2/2011 | Li et al. |
| 7,905,724 B2 | 3/2011 | Kuo et al. |
| 7,914,283 B2 | 3/2011 | Kuo |
| 7,947,508 B2 | 5/2011 | Tricca et al. |
| 8,152,518 B2 | 4/2012 | Kuo |
| 8,172,569 B2 | 5/2012 | Matty et al. |
| 8,235,715 B2 | 8/2012 | Kuo |
| 8,292,617 B2 | 10/2012 | Brandt et al. |
| 8,337,199 B2 | 12/2012 | Wen |
| 8,401,686 B2 | 3/2013 | Moss et al. |
| 8,517,726 B2 | 8/2013 | Kakavand et al. |
| 8,562,337 B2 | 10/2013 | Kuo et al. |
| 8,641,414 B2 | 2/2014 | Borovinskih et al. |
| 8,684,729 B2 | 4/2014 | Wen |
| 8,708,697 B2 | 4/2014 | Li et al. |
| 8,758,009 B2 | 6/2014 | Chen et al. |
| 8,771,149 B2 | 7/2014 | Rahman et al. |
| 8,864,493 B2 | 10/2014 | Leslie-Martin et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,119,691 B2 | 9/2015 | Namiranian et al. |
| 9,161,823 B2 | 10/2015 | Morton et al. |
| 9,241,774 B2 | 1/2016 | Li et al. |
| 9,326,831 B2 | 5/2016 | Cheang |
| 9,433,476 B2 | 9/2016 | Khardekar et al. |
| 9,610,141 B2 | 4/2017 | Kopelman et al. |
| 9,655,691 B2 | 5/2017 | Li et al. |
| 9,662,274 B2 | 5/2017 | Boe |
| 9,675,427 B2 | 6/2017 | Kopelman |
| 9,700,385 B2 | 7/2017 | Webber |
| 9,744,001 B2 | 8/2017 | Choi et al. |
| 9,844,424 B2 | 12/2017 | Wu et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,336,102 B2 | 7/2019 | Cole |
| 10,363,116 B2 | 7/2019 | Boronkay |
| 10,383,705 B2 | 8/2019 | Shanjani et al. |
| D865,180 S | 10/2019 | Bauer et al. |
| 10,449,016 B2 | 10/2019 | Kimura et al. |
| 10,463,452 B2 | 11/2019 | Matov et al. |
| 10,470,847 B2 | 11/2019 | Shanjani et al. |
| 10,517,701 B2 | 12/2019 | Boronkay |
| 10,537,406 B2 | 1/2020 | Wu et al. |
| 10,537,463 B2 | 1/2020 | Kopelman |
| 10,548,700 B2 | 2/2020 | Fernie |
| 10,555,792 B2 | 2/2020 | Kopelman et al. |
| 10,588,776 B2 | 3/2020 | Cam et al. |
| 10,613,515 B2 | 4/2020 | Cramer et al. |
| 10,639,134 B2 | 5/2020 | Shanjani et al. |
| 10,743,964 B2 | 8/2020 | Wu et al. |
| 10,758,323 B2 | 9/2020 | Kopelman |
| 10,781,274 B2 | 9/2020 | Liska et al. |
| 10,813,720 B2 | 10/2020 | Grove et al. |
| 10,874,483 B2 | 12/2020 | Boronkay |
| 2002/0139376 A1 | 10/2002 | Waddy |
| 2002/0192617 A1 | 12/2002 | Phan et al. |
| 2003/0008259 A1 | 1/2003 | Kuo et al. |
| 2003/0065048 A1 | 4/2003 | Paul |
| 2004/0166462 A1 | 8/2004 | Phan et al. |
| 2004/0166463 A1 | 8/2004 | Wen et al. |
| 2005/0014105 A1 | 1/2005 | Abolfathi et al. |
| 2005/0113510 A1 | 5/2005 | Feldstein et al. |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0068353 A1 | 3/2006 | Abolfathi et al. |
| 2006/0078841 A1 | 4/2006 | Desimone et al. |
| 2006/0115782 A1 | 6/2006 | Li et al. |
| 2006/0115785 A1 | 6/2006 | Li et al. |
| 2006/0199142 A1 | 9/2006 | Liu et al. |
| 2006/0234179 A1 | 10/2006 | Wen et al. |
| 2006/0263595 A1 | 11/2006 | Scheubner |
| 2007/0048347 A1 | 3/2007 | Bardach et al. |
| 2007/0298381 A1 | 12/2007 | Collodoro |
| 2008/0003541 A1 | 1/2008 | Leslie-Martin |
| 2008/0118882 A1 | 5/2008 | Su |
| 2008/0120878 A1 | 5/2008 | Smith |
| 2008/0138767 A1 | 6/2008 | Kuo et al. |
| 2008/0160473 A1 | 7/2008 | Li et al. |
| 2008/0182218 A1 | 7/2008 | Chen et al. |

(56) References Cited

U.S. PATENT DOCUMENTS

| | | |
|---|---|---|
| 2008/0268400 A1 | 10/2008 | Moss et al. |
| 2008/0286716 A1 | 11/2008 | Sherwood |
| 2008/0286717 A1 | 11/2008 | Sherwood |
| 2008/0300824 A1 | 12/2008 | Culp et al. |
| 2009/0280450 A1 | 11/2009 | Kuo |
| 2010/0055635 A1 | 3/2010 | Kakavand |
| 2010/0129763 A1 | 5/2010 | Kuo |
| 2011/0189624 A1 | 8/2011 | Wong |
| 2011/0269092 A1 | 11/2011 | Kuo et al. |
| 2014/0067334 A1 | 3/2014 | Kuo |
| 2015/0265376 A1 | 9/2015 | Kopelman |
| 2015/0366637 A1 | 12/2015 | Kopelman et al. |
| 2015/0366638 A1 | 12/2015 | Kopelman et al. |
| 2016/0106521 A1 | 4/2016 | Tanugula et al. |
| 2016/0193014 A1 | 7/2016 | Morton et al. |
| 2016/0242870 A1 | 8/2016 | Matov et al. |
| 2016/0242871 A1 | 8/2016 | Morton et al. |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007362 A1 | 1/2017 | Chen et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007386 A1 | 1/2017 | Mason et al. |
| 2017/0135792 A1 | 5/2017 | Webber |
| 2017/0135793 A1 | 5/2017 | Webber et al. |
| 2017/0165032 A1 | 6/2017 | Webber et al. |
| 2017/0319296 A1 | 11/2017 | Webber et al. |
| 2018/0000564 A1 | 1/2018 | Cam et al. |
| 2018/0140516 A1 | 5/2018 | Rajaiah et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0168776 A1 | 6/2018 | Webber |
| 2018/0243051 A1 | 8/2018 | Stemmer et al. |
| 2018/0353264 A1 | 12/2018 | Riley et al. |
| 2018/0360567 A1 | 12/2018 | Xue et al. |
| 2018/0368944 A1 | 12/2018 | Sato et al. |
| 2019/0000592 A1 | 1/2019 | Cam et al. |
| 2019/0000593 A1 | 1/2019 | Cam et al. |
| 2019/0021817 A1 | 1/2019 | Sato et al. |
| 2019/0029775 A1 | 1/2019 | Morton et al. |
| 2019/0046297 A1 | 2/2019 | Kopelman et al. |
| 2019/0069975 A1 | 3/2019 | Cam et al. |
| 2019/0099129 A1 | 4/2019 | Kopelman et al. |
| 2019/0125494 A1 | 5/2019 | Li et al. |
| 2019/0125497 A1 | 5/2019 | Derakhshan et al. |
| 2019/0152152 A1 | 5/2019 | O'Leary et al. |
| 2019/0175304 A1 | 6/2019 | Morton et al. |
| 2019/0231477 A1 | 8/2019 | Shanjani et al. |
| 2019/0262101 A1 | 8/2019 | Shanjani et al. |
| 2019/0298494 A1 | 10/2019 | Webber et al. |
| 2019/0314119 A1 | 10/2019 | Kopelman et al. |
| 2019/0338067 A1 | 11/2019 | Liska et al. |
| 2019/0343606 A1 | 11/2019 | Wu et al. |
| 2020/0000553 A1 | 1/2020 | Makarenkova et al. |
| 2020/0086553 A1 | 3/2020 | Mojdeh et al. |
| 2020/0100864 A1 | 4/2020 | Wang et al. |
| 2020/0100865 A1 | 4/2020 | Wang et al. |
| 2020/0100866 A1 | 4/2020 | Medvinskaya et al. |
| 2020/0100871 A1 | 4/2020 | Wang et al. |
| 2020/0155276 A1 | 5/2020 | Cam et al. |
| 2020/0188062 A1 | 6/2020 | Kopelman et al. |
| 2020/0214598 A1 | 7/2020 | Li et al. |
| 2020/0214801 A1 | 7/2020 | Wang et al. |
| 2020/0390523 A1 | 12/2020 | Sato et al. |

FOREIGN PATENT DOCUMENTS

| | | |
|---|---|---|
| KR | 20150141076 A | 12/2015 |
| KR | 20190001228 A | 1/2019 |
| WO | WO-2007133850 A1 | 11/2007 |

DURABLE ORNAMENTAL INDICIA CARRIER

RELATED APPLICATIONS

This application claims the benefit of U.S. Provisional Application No. 62/901,091, filed Sep. 16, 2019, which application is incorporated herein by reference.

BACKGROUND

Prior approaches to providing oral appliances with appropriate ornamental aspects can be less than ideal in at least some respects. Objects placed in the mouth should be biocompatible and the mouth can present a challenging environment for materials in at least some respects. At least some of the prior approaches to inkjet printing can be less than ideally suited for oral applications.

Ultraviolet light cured (UV) inkjet printing is a digital printing technology that is gaining popularity in recent years due to its combination of high speed, reliability, high image quality and exceptional image durability. UV inkjet printing can be useful for decorating thin plastic films since it does not require special coatings or layers, operates at low temperatures and prints without any mechanical impact to the substrate.

Typical UV inkjet inks have very low viscosity to be jetted through the small nozzles of the printhead. In order to achieve this, UV inkjet inks may contain a low molecular weight reactive monomer and low molecular weight photoinitiator. After jetting through the printhead the monomer is polymerized and hardens on the print substrate when exposed to UV light. In general, the polymerization reaction does not convert all the monomer and photoinitiator, leaving the unreacted portion to easily migrate to the surrounding environment. In at least some instances, the composition of these monomers and photoinitiators can be regarded as unsafe for human consumption and their use may be limited to applications such as food packaging or medical device decoration. UV inkjet inks referred to as low migration inks are available as an alternative and are designed to limit potential migration of residual ink compounds. They typically use a combination of highly reactive yet low viscosity monomers and photoinitiators that are diffusion hindered. This combination can provide a high degree of polymerization with decreased levels of extractable compounds and can be used for food-safe packaging decoration.

At least some of the prior approaches can be less than ideally suited for use with oral appliances. Decorating irregularly shaped articles such as dental appliances can rely on a thin, flexible and conformable film as the image carrier. However, handling such films during printing and subsequent converting steps can limit the type of film that can be used, and at least some of the prior films are less than ideally suited for use with oral appliances.

One potential challenge associated with UV inks is that oxygen inhibition can result in less than ideal curing. Due to the relatively low viscosity of UV inks, they can be especially prone to oxygen inhibition, which may slow the cure response of the ink. To overcome this, one prior approach has been for an inkjet ink to contain higher levels of photoinitiators to enable a sufficiently cured ink film to be produced. However, such high concentrations of photoinitiators could potentially decrease the food safe nature of the ink and the final properties of the cured ink.

In light of the above, there is a need for improved methods and apparatus for use with oral appliances.

SUMMARY

In some embodiments, the ornamental indicia carrier comprises an ultraviolet light ("UV") cured ink printed on a thin flexible film and combined with an adhesive layer. The ornamental indicia carrier can be configured for use with a mouth for an extended period of time and can be used in conjunction with a dental appliance.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed surface printed ornamental indicia carriers can be used with many objects such as oral appliances. Examples of suitable oral appliances include, sports guards, mouthpieces, aligners, tooth positioners, retainers, apnea devices, jaw repositioning devices, and palatal expanders. Although reference is made to oral appliances, the presently disclosed ornamental carriers can be used with many objects in addition to oral appliances.

Figure 1:
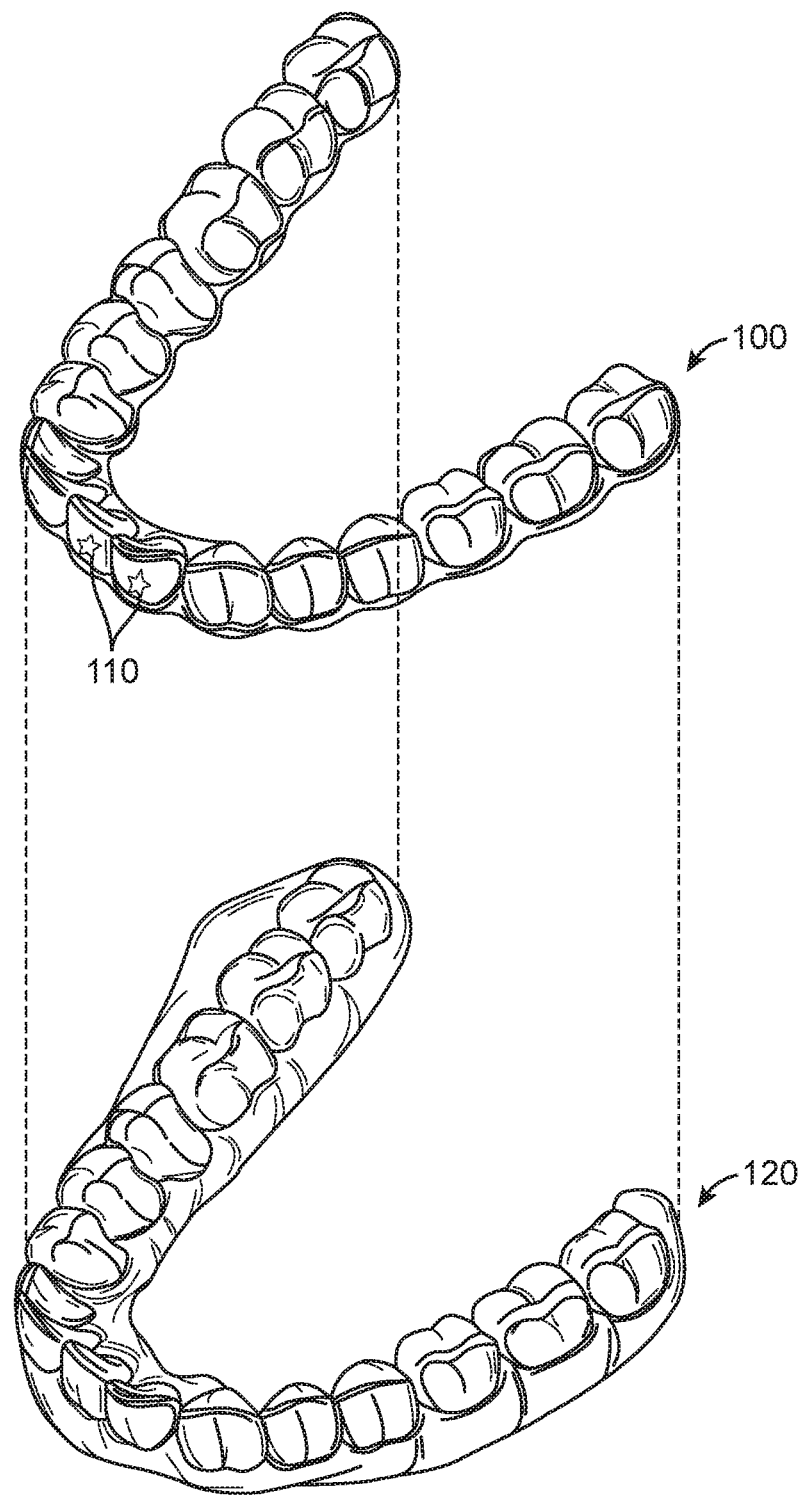
FIG. 1 shows an oral appliance and a surface printed ornamental indicia carrier, in accordance with some embodiments.

FIG. 1 shows an oral appliance 100 and one or more surface printed ornamental indicia carriers 110 placed on the appliance. The appliance 100 can be configured to fit over an entire dental arch 120. In other embodiments, the dental appliance may be designed to fit over some or all of the teeth in the upper or lower jaw. The dental appliance 100 can be fabricated from a polymeric shell, or formed from another material, and include a number of cavities shaped to receive corresponding teeth. Aligners for positioning teeth are commercially available from Align Technology.

In some embodiments, a dental appliance can include a multi-layer material having a first layer with a first elastic modulus and a second layer with a second elastic modulus less than the first elastic modulus. A dental appliance can also include various combinations of materials, including alternating configurations of hard and soft material (e.g., hard, soft, hard material combinations; soft, hard, soft material combinations; etc.). Suitable polymeric materials for a first polymer layer can include a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate or a combination thereof (e.g., a blend of at least two of the listed hard polymeric materials). In some embodiments, a first polymer layer of a dental appliance can include polymeric materials, such as a polycarbonate, a co-polyester, a polyester, and a thermoplastic polyurethane. In some embodiments, a first layer can be composed of multiple layers, e.g., two or three polymer layers co-extruded to form one layer.

A first polymer layer can have a variety of physical properties that can, e.g., improve treatment options for a practitioner. For example, physical properties such as tensile strength, elongation at yield, elongation at break, tensile modulus, flexural modulus, stress relaxation over time, and light transmission can each be specifically tailored for a particular application. In some embodiments, a first polymer layer of the appliances can have a physical property of at least one of a tensile strength at yield of between about 4000 pounds per square inch (psi) and 6500 psi, an elongation at yield of greater than about 4%, an elongation at break of greater than about 70%, a tensile modulus of greater than about 150,000 psi, a flexural modulus greater than about 150,000 psi, a stress relaxation at 24 hours testing in a wet environment (e.g., between about 90%-100% relative humidity) is greater than 10%, and a light transmission between 400 nm and 800 nm of greater than about 75%.

Suitable polymeric materials for a second polymer layer can include a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or a combination thereof (e.g., a blend of at least two of the listed polymeric materials). The second polymer layers can be the same material or a different material. In certain embodiments, different layers in a dental appliance are the same polymeric material.

A second polymer can have a variety of physical properties. For example, physical properties such as hardness, ultimate tensile strength, elongation at break, tensile modulus, compression set, flexural modulus, and light transmission can each be specifically tailored for a particular application. In some embodiments, a second polymer layer can independently have a physical property of at least one of a hardness of about 60 A to about 85 D, an ultimate tensile strength of greater than about 5000 psi, an elongation at break of greater than about 200%, a compression set at about 70° C. of greater than 40% after 24 hours, a flexural modulus of greater than about 35,000 psi, and a light transmission between 400 nm and 800 nm of greater than about 75%.

As described herein, the layers of the appliances can include a first polymer layer disposed between two second polymer layers. In one embodiment, the multilayer appliances can include a first polymer layer of one type of material (e.g., a co-polyester), and two second polymer layers of other types of material that can be the same or different (e.g., two second polymer layers of thermoplastic polyurethane elastomer). In some embodiments, the multilayer appliances can also include a first polymer layer of at least two layers of polymer material. For example, the first polymer layer can include several polymer layers laminated together to form the first polymer layer. The laminated first polymer layer can include at least two layers of any combination of the following polymer materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and a polytrimethylene terephthalate. Similarly, in some embodiments, the multilayer appliances can include a second polymer layer of at least two layers of polymer material. In some embodiments, the layers of an appliance can include a second polymer layer disposed between two first polymer layers. Any of the foregoing materials can be used for this combination.

The one or more ornamental indicia carriers 110 can be placed at any suitable location of the oral appliance 100. The ornamental indicia carrier 110 comprises suitable materials for use with an oral appliance 100. Although reference is made to UV curable inks, other print techniques can be used such as water based inks or solvent based inks.

In some embodiments, the ornamental carrier 110 comprises a polyolefin film to provide a combination of clarity, flexibility and robustness suitable for use with appliances. For example, oriented polyolefin films such as biaxially oriented polypropylene (BOPP) films can be used as thin gauge, high clarity and conformable films for decorating objects such as oral appliances. As a thin film, BOPP films have an appropriate stiffness in the machine direction during printing to decrease stretching of the film when moving through rollers of a printing press. These films can also have coextruded skin layers that can be corona treated to improve print adhesion, in some instances without requiring an additional top-coat layer.

In accordance with embodiments of the present disclosure, a non-contact printing process such as inkjet printing can be used with thin BOPP films with thickness in the range of 35 microns to 60 microns that can be handled through the process without substantial stretching or web breaking.

The inks can be configured to match the BOPP film, printhead, UV curing system and other elements of the printing system and process. The process of designing a finely tuned ink system can involve refining the printed image quality with good physical properties such as adhesion, flexibility and scratch resistance. Based on the teachings disclosed herein, one or ordinary skill in the can design an ink system to deliver a high-quality indelible marking of the indicia with appropriate durability.

In some embodiments, incomplete curing of the ink can be addressed by applying first a UV ink followed by an overprint varnish (OPV) and curing. This approach enables UV inks with lower levels of photoinitiator to be used. This can be achieved by applying an OPV layer (preferably UV curable) onto a previously partially cured ink layer, and then exposing the combined ink-OPV bi-layer to further UV irradiation. The OPV and ink can be formulated in such a way that applying them on top of each other allows the partially cured ink to become fully cured when protected from atmospheric oxygen by the overlaying OPV. In some embodiments, the ink of the OPV bilayer is exposed to a second dose of UV-irradiation that results in further radical generation throughout the underlying ink layer resulting in further conversion of unreacted monomer. In some embodiments, an in-line process for the preparation of decorative indicia by the ink-OPV combination encompasses the deposition of the ink component first, with subsequent preliminary (or 'pinning') UV-cure, followed by the deposition of the OPV component, with subsequent cure of the ink-OPV layer with a suitable dose of UV-light. In some embodiments, the OPV component also provides functionality that may not be readily achievable by the inks alone. For example, the OPV can be modified to provide the required slip, abrasion resistance, chemical resistance required of the printed ink-OPV combination.

In some embodiments, an alternate way to achieve indelible marking of indicia is by printing a mirror or reverse image that is visible through the clear flexible film. This approach may decrease the need for an OPV to protect the surface printed inks. Such reverse printed indicia can be produced by printing on the thin BOPP film as described herein, applying the adhesive to the printed side of the film over the ink and laminating the combination to a pre-silicone-coated polymeric film or paper liner. Reverse printed indicia can be further combined with white ink printed over the reverse image to create an opaque background which enhances the color density and graphic quality of the printed indicia. In some embodiments, the opaque background color may not be white. In some embodiment, the opaque background may have a color selected to match the color and a patient's teeth. In some embodiment, the opaque background may have a color selected within a range of human tooth colors.

Thin flexible BOPP film printed with UV inkjet inks in either surface printed or reverse printed format can be subsequently combined with a pressure sensitive adhesive that adheres well to a variety of materials typically used in medical and dental devices. In some embodiments, the pressure sensitive adhesive is a high tack synthetic rubber-based transfer adhesive designed for medical device applications and is approved for use on skin.

In some embodiments, an ornamental indicia carrier can remain durably adhered to a dental appliance "Durably adhered," as used herein, may refer to an adherence property of a material (e.g., an ornamental indicia carrier). Durably adhered, as used herein, may refer to a material remaining adhered to a surface, even under humid and/or wet conditions, and being able to withstand abrasive, rubbing, and/or other mechanical forces. Whether a material is durably adhered to another can be assessed by any number of tests, including abrasiveness tests and/or liquid immersion tests (e.g., water immersion tests). In some embodiments, a process that results in an ornamental indicia carrier remaining adhered at a desired level, such as greater than 75%, greater than 90%, greater than 95%, greater than 99%, or 100%, after a 24 hour water immersion test, including for water at a temperature corresponding to the oral cavity, may be characterized as durably adhered, including for a standard adhesive test such as by a tape test.

"High humidity" or "wet environment," as used herein may refer to environments having a substantial liquid aspect. For example, the oral cavity of a living animal, including a human, may be considered herein to be a high humidity and a wet environment. Immersion, total or partial, in a liquid may also be considered a wet environment.

Unless explicitly defined otherwise, "substantial," as used herein, may refer to a value that is within at least 20%, within at least 10%, or within at least 5% of a desired value, or that is equal to a value.

"Soak time," as used herein, may refer to the time elapsed between ink application/contact with the substrate and the process of curing. A precise soak time may depend on process conditions and material variables, including temperature, ink composition, material composition and/or shape (e.g., adhesive composition and/or shape), for example. Similarly, an application of interest in which an ornamental indicia carrier will be used may influence soak time. For example, applications requiring stronger adhesion may have a longer soak time than applications where a lesser adhesive force is suitable.

"Operably coupled," as used herein, may refer to a configuration between two or more components such that the functionality of each component is maintained. Operably coupled may include configurations in which components are directly connected to each other as well as configurations where components are indirectly connected to one.

"Polymer," as used herein, may refer to a molecule composed of repeating structural units connected by covalent chemical bonds often characterized by a substantial number of repeating units (e.g., equal to or greater than 3 repeating units, optionally, in some embodiments equal to or greater than 10 repeating units, in some embodiments greater or equal to 30 repeating units) and a high molecular weight (e.g. greater than or equal to 10,000 Da, in some embodiments greater than or equal to 50,000 Da or greater than or equal to 100,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Useful polymers include organic polymers or inorganic polymers that may be in amorphous, semi-amorphous, crystalline or semi-crystalline states.

"Polymer network," as used herein, may refer to a polymer composition comprising a plurality of polymer chains wherein a large portion (e.g., >80%) and optionally all the polymer chains are interconnected, for example via covalent crosslinking, to form a single polymer composition. In an embodiment, there is provided a radiopaque polymer in the form of a crosslinked network in which at least some of the crosslinks of the network structure are formed by covalent bonds.

"Monomer," as used herein, may refer to a reagent which can undergo polymerization under one or more specified conditions. A monomer reagent may comprise at least one monomer molecule, where a monomer molecule is a molecule which can undergo polymerization, thereby contributing constitutional units to the structure of a macromolecule or oligomer. In an embodiment, a monomer reagent may be represented by an average or dominant chemical structure and comprise monomer molecules having that chemical structure but may also contain components with other chemical structures. For example, a monomer reagent may comprise impurities having chemical structures other than the average or dominant structure of the reagent. An oligomer or oligomeric reagent is also a reagent which can undergo polymerization under appropriate conditions. An oligomeric reagent comprises an oligomer molecule, the oligomer molecule comprising a small plurality of units derived from molecules of lower relative molecular mass. In an embodiment, certain hyperbranched crosslinking reagents suitable for use with the invention may be regarded as oligomeric reagents.

The term "biocompatible" refers to a material that does not cause immune rejection or detrimental effect, which is referred to herein as an adverse immune response, when disposed within an in vivo biological environment. For example, In embodiments, a biological marker indicative of an immune response changes less than 10%, or less than 20%, or less than 25%, or less than 40%, or less than 50% from a reference value. when a human or animal is exposed to or comes into contact with the biocompatible material. Alternatively, the immune response can be determined histologically, in which the localized immune response is assessed by means of visual assessment markers, which include immune cells or markers that are involved in the path of the immune response, in and adjacent to the material. In one aspect, a biocompatible material or device does not observably change the immune response as determined histologically. In some embodiments, the present invention provides biocompatible devices configured for long-term use, such as on the order of weeks to months, without invoking an adverse immune response. Biological effects can be initially assessed by measuring cytotoxicity, sensitization, irritation and intracutaneous reactivity, acute systemic toxicity, pyrogenicity, subacute/subchronic toxicity and/or implantation. Biological tests for supplemental evaluation include tests for chronic toxicity.

Figure 2A:
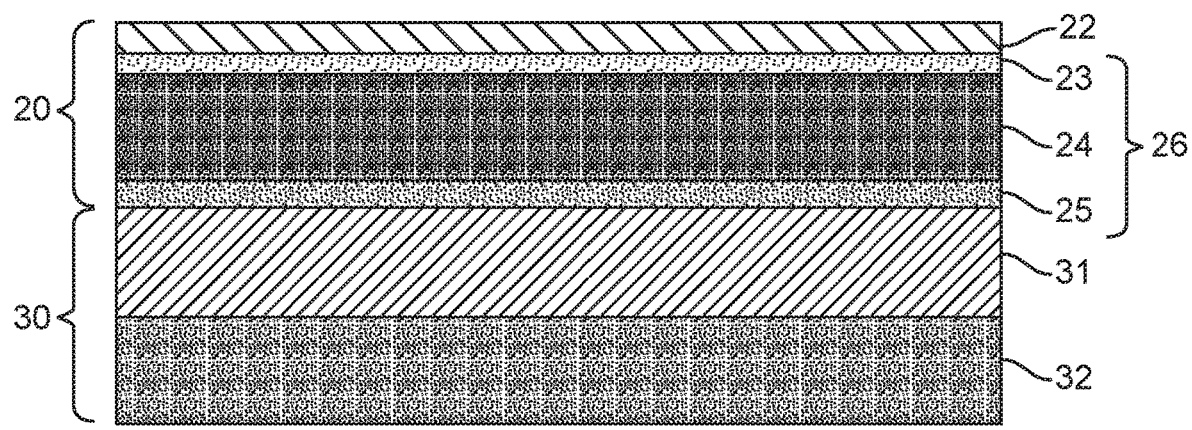
FIG. 2A shows a cross section of a surface printed ornamental indicia carrier, in accordance with some embodiments.

A surface printed ornamental indicia carrier as shown in FIG. 2A. The carrier comprises a top print laminate 20 and a bottom adhesive laminate 30. In some embodiments, the top print laminate 20 comprises an oriented print layer 26. The orientated print layer 26 comprises a core layer 24, a first adhesion layer 23 and a second adhesion layer 25. The print layer 26 comprises a thickness within a range from 10 µm to 100 µm, and preferably 30 µm to 70 µm, for example from 35 µm to 60 µm. The print layer 26 may be made from Biofilm Bioseal-TSI Product CC4535, 35 µm transparent coextruded BOPP film sold by Taghleef Industries, Newark, Del. or Transprop HSCT1-F, 60 µm coextruded two side heat sealable BOPP film sold by Transcendia, Franklin Park, Ill. The first adhesion layer 23 extends over the core layer 24 and can extend fully contiguous over one surface of the core layer 24. The second adhesion layer 25 extends along a second surface of the core layer 24. In some embodiments, the exposed surface of the first adhesion layer is treated to enhance print adhesion. For example, the surface treatment may comprise one or more methods such as corona, flame or plasma treatment techniques.

The treated surface may then be decorated by an ink layer 22 printed using UV inkjet printing. The ink layer 22 can further comprise one or more specific colored inks and an optional white ink to provide opacity in order to enhance color density. The ink layer can be fully or partially contiguous across the surface of the top print laminate. In some embodiments, ink layer 22 is provided using UV inks that are jetted through an inkjet printing system. In some embodiments, ink layer 22 comprises one or more of Epson's LED-cured UV ink with digital varnish and high opacity white ink printed using an Epson SurePress L-6034VW from Epson America, Long Beach, Calif., or Amica's NuviINK single-pass series UV inks printed using an Amica LR54 full color inkjet web press from Amica Systems, Irvine, Calif.

In some embodiments, the bottom laminate 30 comprises a pressure sensitive adhesive layer 31 and a removable protective liner 32 over a surface of the pressure sensitive adhesive. In some embodiments, the removable protective liner 32 comprises a silicone coated release paper. The removable protector may be divided into two or more pieces. In some embodiments, at least one of the protector pieces is significantly larger than the other or others and covers a major proportion of the adhesive layer. In some embodiments, the suitable removable protective liner 32 comprises a bleached Kraft paper with silicone coated on one or both sides. In some embodiments, the removable protective liner 32 comprises a thickness within a range from 100 µm to 200 µm, and preferably from 80 µm to 150 µm, for example 90 µm.

In some embodiments, the ornamental indicia carrier is constructed such that the adhesion layer 25 of the top print laminate is facing and in contact with the pressure sensitive adhesive layer 31 of the bottom adhesive laminate. In some embodiments, the top laminate 20 and adhesive laminate 30 are fully contiguous across their interface. The pressure sensitive adhesive layer 31 may be formed from an adhesive which is suitable for contact with the skin. The pressure sensitive adhesive may comprise a high tack synthetic rubber-based transfer adhesive designed for medical device applications and approved for use on skin. The pressure sensitive adhesive layer 31 may also be sufficiently clear to see through to the dental appliance surface. The pressure sensitive adhesive layer 31 has thickness within a range from 50 µm to 200 µm, preferably 80 to 150 µm, for example from 50 µm to 110 µm. In some embodiments, the pressure sensitive adhesive layer 31 includes 3M Product 1504XL sold by 3M Medical Specialties, St. Paul, Minn.; Polyken 3426A sold by Berry Plastics, Franklin, Mass.

Figure 2B:
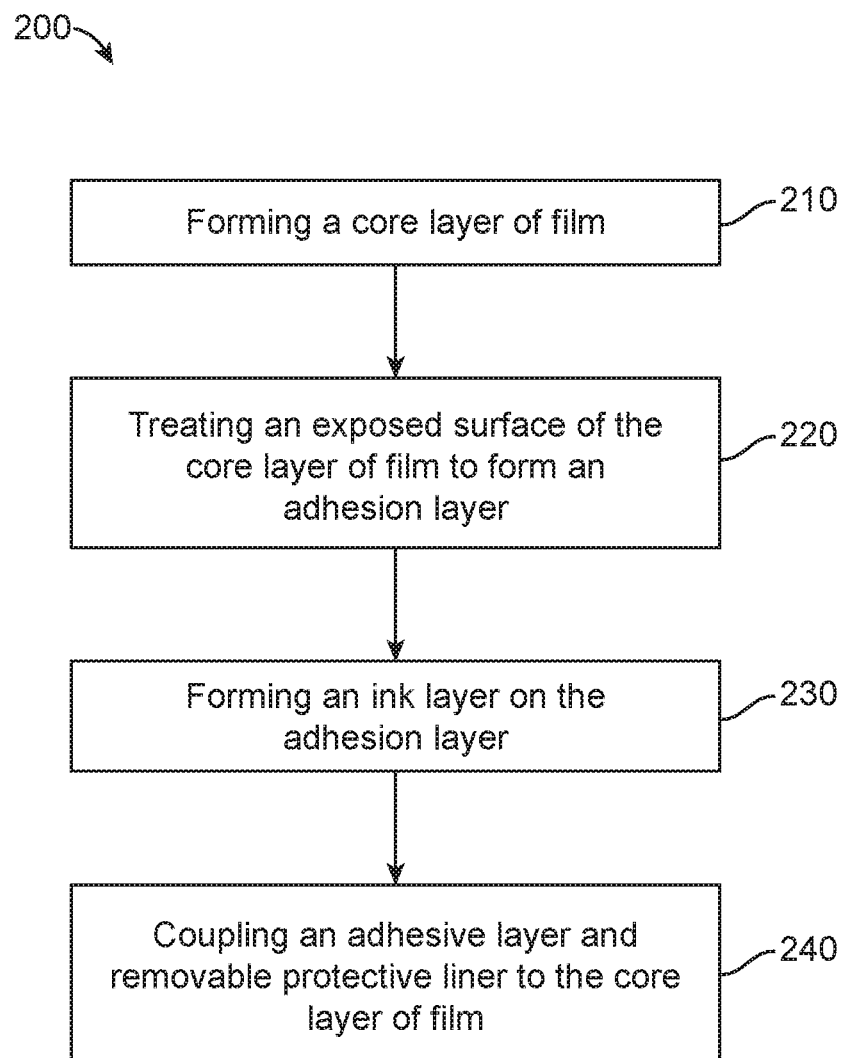
FIG. 2B shows a method of fabricating the surface printed ornamental indicia carrier of FIG. 2A, in accordance with some embodiments.

FIG. 2B shows a method 200 of fabricating a printed ornamental indicia carrier. At block 210 a core layer of film is formed. In some embodiments, the core layer of film, such as the biaxially oriented polypropylene (BOPP) film, may be formed using a tubular process or a tenter frame process to stretch the film in both a machine and transverse direction. In some embodiments, the core layer of film may be provided to or otherwise received by a printing or fabrication machine for use in the fabrication of the printed ornamental indicia carrier.

At block 220 an adhesion layer is formed on a surface of the core layer. The adhesion layer may be formed on an external or outer surface of the core layer of film. In some embodiments, the adhesion layer is a surface treatment of the core layer of film. A surface treatment may include treatments to enhance ink and print adhesion on the surface of the core layer film. The surface treatment may include one or more of corona, flame or plasma treatment techniques to prepare the surface receiving the ink layer. The surface treatment process may cause the molecular chains of the surface polymers to be broken into allow polar functional groups to be added to the broken chains, thereby creating an outer surface that is more suitable for receiving ink and for coupling to adhesives.

At block 230 an ink layer is formed on the adhesion layer. The ink layer may be formed by inkjet printing a UV curable ink onto the adhesion layer. The ink layer may comprise one or more inks. In some embodiments the ink layer may include multiple layers of ink. For example, a first one or more layers of ink may include a mixture of the primary ink pigments to create a color image and a second one or more layers may include a base layer of white in order to provide opacity into enhance the color density of the indicia. In a front printed indicia, such as shown in FIG. 2A, the base layer may be printed before the one or more color layers. In some embodiments, a UV curing step may occur between each printing operation. For example, after each layer is printed, that layer is cured using UV light. In some embodiments, the UV curing step occurs only after all the ink layers are printed. In some embodiments, the base layer is cured after it is printed and then the ink layers are printed on top of the cured base layer and finally, the ink layers are cured.

At block 240 an adhesion layer and a protective liner are coupled to the core layer of film. In some embodiments, a laminate layer comprising a pressure sensitive adhesive layer and a removable protective liner are coupled, as a unit, to the laminate layer. In some embodiments the pressure sensitive adhesive layer may be applied to the core layer first and then the laminate layer may be applied to the pressure sensitive adhesive layer.

Although the blocks of method 200 are depicted as taking place in sequential order, in some embodiments, the order of the blocks may be arranged differently. For example, the adhesion layer and the protective liner layer may be coupled to the core layer before the ink is printed and cured on the core layer.

Figure 3A:
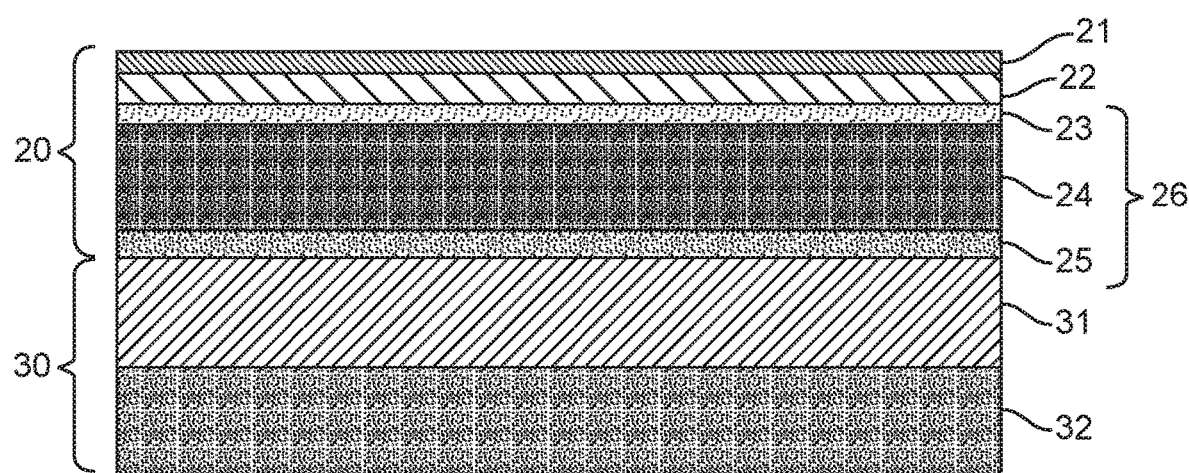
FIG. 3A shows a cross section of a surface printed ornamental indicia carrier with over print varnish, in accordance with some embodiments.

FIG. 3A shows a surface printed ornamental indicia carrier comprising a top print laminate 20 and an adhesive laminate 30. The top print laminate 20 comprises an oriented print layer 26. The oriented print layer 26 comprises a core layer 24, a first adhesion layer 23 and a second adhesion layer 25. The first adhesion layer 23 extends along the core layer 24 and can be fully contiguous over a surface of the core layer. The second adhesion layer 25 extends along a second surface of the core layer 24. In some embodiments, the exposed surface of the first adhesion layer is further treated to enhance print adhesion. The treated surface can then be decorated by ink layer printed using UV inkjet printing. The ink layer can be fully or partially contiguous across the surface of the top print laminate. A clear overprint varnish (OPV) is then applied over the UV ink to encapsulate the image areas on the surface. The clear OPV can be fully or partially contiguous across the image area so as to encapsulate the UV ink, for example so as to fully encapsulate the UV ink. The clear OPV can be applied by one or more techniques such as direct coating, transfer coating or printing. In some embodiments the OPV layer is printed, for example by in-line UV inkjet printing. In some embodiments, the OPV layer is present only in the areas where the ink layer is present. The bottom laminate 30 comprises of a pressure sensitive adhesive layer 31 and a removable protective liner 32 extending over a surface of the pressure sensitive adhesive layer 31. The ornamental indicia carrier can be constructed such that the adhesion layer 25 of the top print laminate is facing and in contact with the pressure sensitive adhesive layer 31 of the bottom adhesive laminate. In some embodiments, the top laminate 20 and bottom laminate 30 are fully contiguous across their interface.

In some embodiments, the pressure sensitive adhesive layers 31 may preferably be formed from an adhesive which is configured for contact with the skin. The pressure sensitive adhesive can be a high tack synthetic rubber-based transfer adhesive designed for medical device applications and is approved for use on skin. In some embodiments, the pressure sensitive adhesive layer 31 is sufficiently clear to see through to the ornamental indicia layer 510. In some embodiments, the pressure sensitive adhesive layer 31 is sufficiently clear to see through to the dental appliance surface. In some embodiments, the pressure sensitive adhesive layer 31 has thickness from 50 to 200 µm, and preferably 80 to 150 µm, for example 50 µm and 110 µm.

In some embodiments, pressure sensitive adhesive layer 31 includes 3M Product 1504XL sold by 3M Medical Specialties, St. Paul, Minn.; or Polyken 3426A sold by Berry Plastics, Franklin, Mass.

Figure 3B:
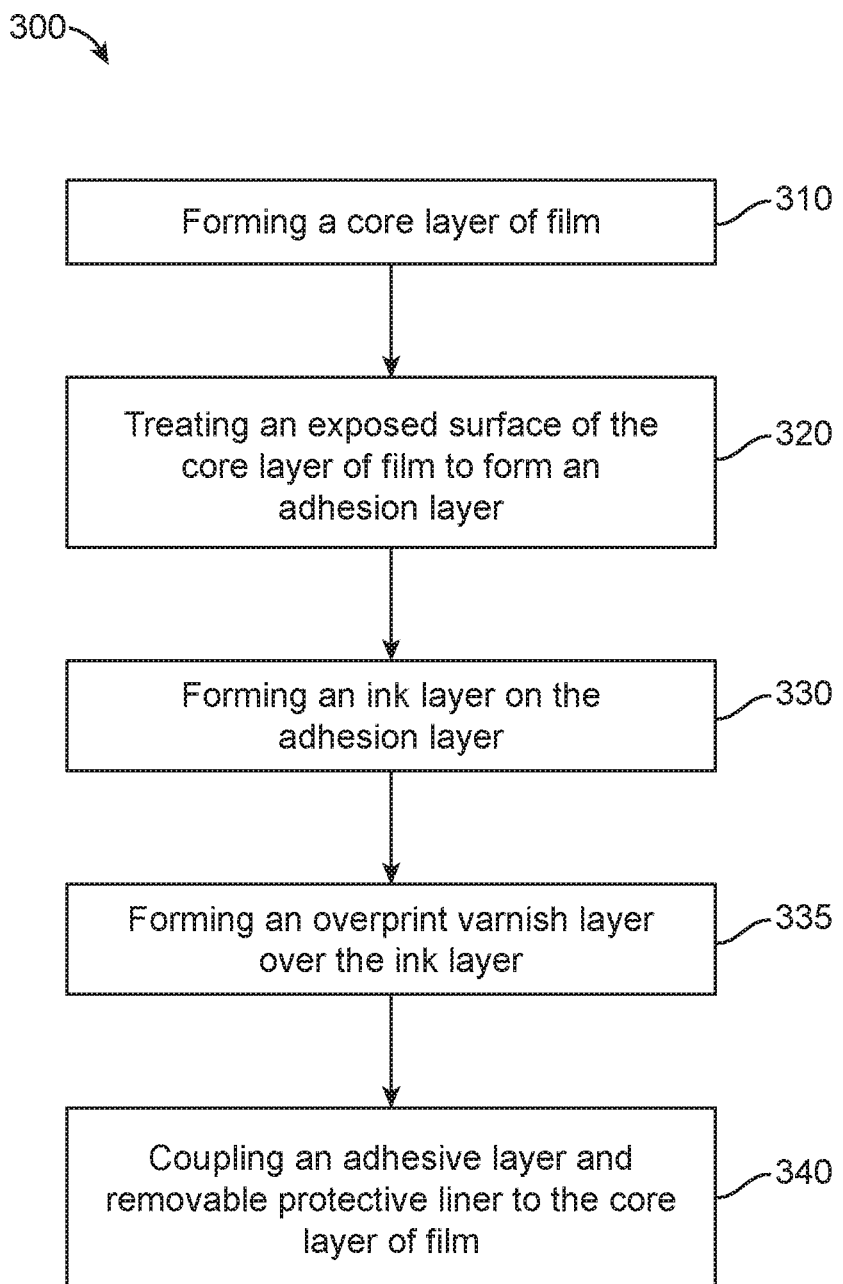
FIG. 3B shows a method of fabricating the surface printed ornamental indicia carrier of FIG. 3A, in accordance with some embodiments.

FIG. 3B shows a method 300 of fabricating a printed ornamental indicia carrier. At block 210 a core layer of film is formed. In some embodiments, the core layer of film, such as the biaxially oriented polypropylene (BOPP) film, may be formed using a tubular process or a tenter frame process to stretch the film in both a machine and transverse direction. In some embodiments, the core layer of film may be provided to or otherwise received by a printing or fabrication machine for use in the fabrication of the printed ornamental indicia carrier.

At block 320 an adhesion layer is formed on a surface of the core layer. The adhesion layer may be formed on an external or outer surface of the core layer of film. In some embodiments, the adhesion layer is a surface treatment of the core layer of film. A surface treatment may include treatments to enhance ink and print adhesion on the surface of the core layer film. The surface treatment may include one or more of corona, flame or plasma treatment techniques to prepare the surface receiving the ink layer. The surface treatment process may cause the molecular chains of the surface polymers to be broken into allow polar functional groups to be added to the broken chains, thereby creating an outer surface that is more suitable for receiving ink and for coupling to adhesives.

At block 330 an ink layer is formed on the adhesion layer. The ink layer may be formed by inkjet printing a UV curable ink onto the adhesion layer. The ink layer may comprise one or more inks. In some embodiments the ink layer may include multiple layers of ink. For example, a first one or more layers of ink may include a mixture of the primary ink pigments to create a color image and a second one or more layers may include a base layer of white in order to provide opacity into enhance the color density of the indicia. In a front printed indicia, such as shown in FIG. 2B, the base layer may be printed before the one or more color layers. In some embodiments, a UV curing step may occur between each printing operation. For example, after each layer is printed, that layer is cured using UV light. In some embodiments, the UV curing step occurs only after all the ink layers are printed. In some embodiments, the base layer is cured after it is printed and then the ink layers are printed on top of the cured base layer and finally, the ink layers are cured.

At block 335 in overprint varnish layer is formed. The overprint varnish layer may be a clear overprint varnish layer that encapsulates the ink image areas on the surface of the core layer. In some embodiments the overprint varnish may be applied to the indicia carrier through one or more of a direct coating, a transfer coating or a printing application. In some embodiments the overprint varnish layer may fully encapsulate the ink printed on the ink layer, while in some embodiments, the overprint varnish layer may be applied only on the areas where the ink layer is present.

In some embodiments, the ink layer is only partially cured before the overprint varnish layer is applied. In some embodiments, the ink layer is at least partially cured, for example fully cured, before the overprint varnish layer is applied and then cured. In some embodiments, the ink layer is at least partially, but not fully cured before the overprint varnish layers applied and then cured. In some embodiments, the ink layer and the overprint varnish layer are at least partially cured at the same time At block 340 an adhesion layer and a protective liner are coupled to the core layer of film. In some embodiments, a laminate layer comprising a pressure sensitive adhesive layer and a removable protective liner are coupled, as a unit, to the laminate layer. In some embodiments the pressure sensitive adhesive layer may be applied to the core layer first and then the laminate layer may be applied to the pressure sensitive adhesive layer.

Although the blocks of method 300 are depicted as taking place in sequential order, in some embodiments, the order of the blocks may be arranged differently. For example, the adhesion layer and the protective liner layer may be coupled to the core layer before the ink is printed in cured on the core layer.

Figure 4A:
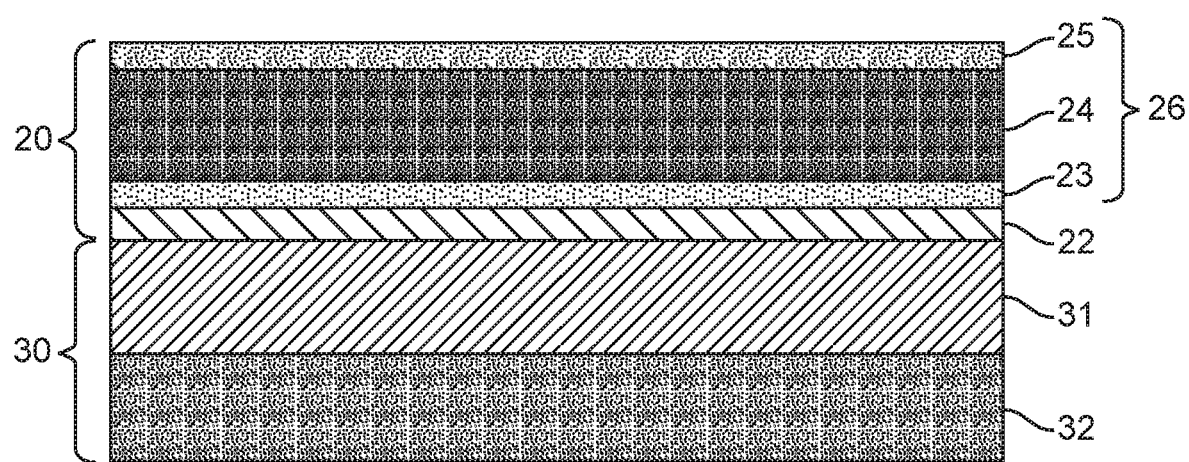
FIG. 4A shows cross section of a reverse printed ornamental indicia carrier, in accordance with some embodiments.

A reverse printed ornamental indicia carrier is shown in FIG. 4A. The reverse printed ornamental indicia carrier comprises a top print laminate 20 and a bottom adhesive laminate 30. The top print laminate 20 comprises an oriented print layer 26. The oriented print layer 26 comprises the core layer 24, the first adhesion layer 23 and the second adhesion layer 25. The first adhesion layer 23 extends along a first surface of the core layer and can be fully contiguous over the first surface of the core layer. The second adhesion layer extends along the second surface of the core layer. In some embodiments, the exposed surface of the first adhesion layer is treated to enhance print adhesion. The treated surface can then be decorated with the ink layer 22, for example by printing the ink layer on the treated surface, such as UV inkjet printing as described herein. The ink layer 22 can be fully or partially contiguous across the surface of the top print laminate. The bottom laminate 30 comprises of a pressure sensitive adhesive layer 31 and a removable protective liner 32 over a surface of the pressure sensitive adhesive layer 31. The ornamental indicia carrier can be constructed such that the ink layer 22 of the top print laminate faces and contacts the pressure sensitive adhesive layer 31 of the bottom adhesive laminate. In some embodiments, the top laminate 20 and bottom laminate 30 are fully contiguous across their interface.

In some embodiments, the adhesion layer 25, the core layer 24 and the adhesion layer 23 are sufficiently clear to allow the ink layer 23 to be seen under these layers.

Figure 4B:
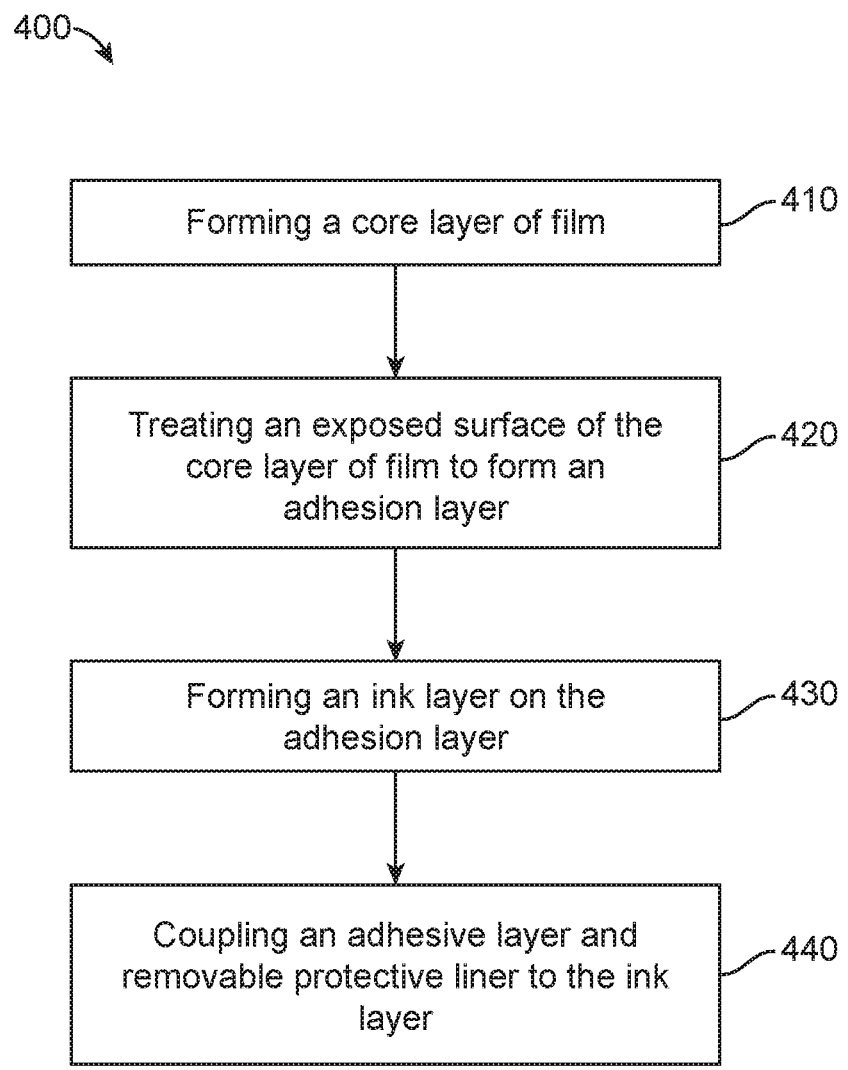
FIG. 4B shows a method of fabricating the surface printed ornamental indicia carrier of FIG. 4A, in accordance with some embodiments.

FIG. 4B shows a method 400 of fabricating a printed ornamental indicia carrier. At block 410 a core layer of film is formed. In some embodiments, the core layer of film, such as the biaxially oriented polypropylene (BOPP) film, may be formed using a tubular process or a tenter frame process to stretch the film in both a machine and transverse direction. In some embodiments, the core layer of film may be provided to or otherwise received by a printing or fabrication machine for use in the fabrication of the printed ornamental indicia carrier.

At block 420 an adhesion layer is formed on a surface of the core layer. The adhesion layer may be formed on an external or outer surface of the core layer of film. In some embodiments, the adhesion layer is a surface treatment of the core layer of film. A surface treatment may include treatments to enhance ink and print adhesion on the surface of the core layer film. The surface treatment may include one or more of corona, flame or plasma treatment techniques to prepare the surface receiving the ink layer. The surface treatment process may cause the molecular chains of the surface polymers to be broken into allow polar functional groups to be added to the broken chains, thereby creating an outer surface that is more suitable for receiving ink and for coupling to adhesives.

At block 430 an ink layer is formed on the adhesion layer. The ink layer may be formed by inkjet printing a UV curable ink onto the adhesion layer. The ink layer may comprise one or more inks. In some embodiments the ink layer may include multiple layers of ink. For example, a first one or more layers of ink may include a mixture of the primary ink pigments to create a color image and a second one or more layers may include a base layer of white in order to provide opacity into enhance the color density of the indicia. In a reverse printed indicia, such as shown in FIG. 4A, the base layer may be printed after the one or more color layers. In some embodiments, a UV curing step may occur between each printing operation. For example, after each ink layer is printed, that ink layer is cured using UV light. In some embodiments, the UV curing step occurs only after all the ink layers are printed. In some embodiments, the ink layer is cured after it is printed and then the base layer is printed on top of the cured ink layer or layers and finally, the ink layers are cured.

At block 440 an adhesion layer and a protective liner are coupled to the ink layer. In some embodiments, a laminate layer comprising a pressure sensitive adhesive layer and a removable protective liner are coupled, as a unit, to the laminate layer. In some embodiments the pressure sensitive adhesive layer may be applied to the core layer first and then the laminate layer may be applied to the pressure sensitive adhesive layer.

Although the blocks of method 400 are depicted as taking place in sequential order, in some embodiments, the order of the blocks may be arranged differently.

In some embodiments, a method of manufacture of the ornamental indicia carrier comprises one or more of the following steps: treating the exposed surface of the adhesion layer 23 using corona treatment; applying the UV ink layer 22 to the treated surface of the adhesion layer 23 with using inkjet printing to provide top print laminate 20; and laminating the top print laminate 20 to the bottom adhesive laminate 30; and cutting the resulting ornamental indicia layer to desired size and shape.

The following additional disclosure is provided in accordance with additional and alternative embodiments as will be appreciated by one of ordinary skill in the art. Each of these is provided as a non-limiting example in accordance with the present disclosure.

In some embodiments, the oriented print layer 26 comprises one or more oriented polyolefin films, such as one or more biaxially oriented polypropylene (BOPP) films.

In some embodiments, the oriented print layer 26 is coextruded with adhesion layers 23 and 25 on two sides of the core layer 24. In some embodiments, the oriented print layer 26 comprises sufficient clarity to see through to the ink layer 22. In some embodiments, the oriented print layer 26 complies with FDA and at least some international regulations related to its use in contact with food articles or skin. In some embodiments, the oriented print layer 26 comprises a thickness within a range from 10 µm to 100 µm, and preferably 30 µm to 70 µm, for example from 35 µm to 60 µm. The oriented print layer 26 may comprise—Biofilm Bioseal-TSI Product CC4535, 35 µm transparent coextruded BOPP film sold by Taghleef Industries, Newark, Del.; or Transprop HSCT1-F, 60 µm coextruded two side heat sealable BOPP film sold by Transcendia, Franklin Park, Ill.

The pressure sensitive adhesive layer 31 may be formed from an adhesive which is suitable for contact with the skin. The pressure sensitive adhesive may comprise a high tack synthetic rubber-based transfer adhesive designed for medical device applications and approved for use on skin. The suitable pressure sensitive adhesive layer 31 can be sufficiently clear to see through to the dental appliance surface. Suitable pressure sensitive adhesive layer 31 has thickness within a range from 50 µm to 200 µm, preferably 80 to 150 µm, for example from 50 µm to 110 µm. In some embodiments, the pressure sensitive adhesive layer 31 includes 3M Product 1504XL sold by 3M Medical Specialties, St. Paul, Minn.; Polyken 3426A sold by Berry Plastics, Franklin, Mass.

In some embodiments, the removable protective liner 32 comprises a silicone coated release paper. The removable protector may be divided into two or more pieces. In some embodiments, at least one of the protector pieces is significantly larger than the other or others and covers a major proportion of the adhesive layer. In some embodiments, the suitable removable protective liner 32 comprises a bleached Kraft paper with silicone coated on one or both sides. In some embodiments, the removable protective liner 32 comprises a thickness within a range from 100 µm to 200 µm, and preferably from 80 µm to 150 µm, for example 90 µm. In some embodiments, ink layer 22 is provided using UV inks that are jetted through an inkjet printing system.

In some embodiments, ink layer 22 comprises one or more of Epson's LED-cured UV ink with digital varnish and high opacity white ink printed using an Epson SurePress L-6034VW from Epson America, Long Beach, Calif.; or Amica's NuviINK single-pass series UV inks printed using an Amica LR54 full color inkjet web press from Amica Systems, Irvine, Calif.

The ornamental indicia carrier may be produced to different sizes to fit various types of dental appliances and placed in a bacteria proof pouch, sealed and sterilized by conventional methods including using ethylene oxide or irradiation.

The carrier may comprise an indicia for identification, such as a barcode or serial number, for example. This can be formed with the ink layer and printing as described herein and can be provided alternatively to an ornamental print pattern on the print layer or in combination with an ornamental print pattern on the print layer.

Ornamental Indicia Carrier with Edible Component

In some embodiments, the ornamental indicia carrier comprises an edible component. The ornamental indicia carrier may comprise an edible colorant applied on an edible carrier, which can be combined with film and adhesive layers as described herein.

The ornamental indicia carrier can be provided using an edible colorant applied on an edible carrier and is further combined with film and adhesive layers. The ornamental indicia carrier can be configured for placement inside the mouth for extended period of time and can be used in conjunction with a dental appliance.

Figure 5A:
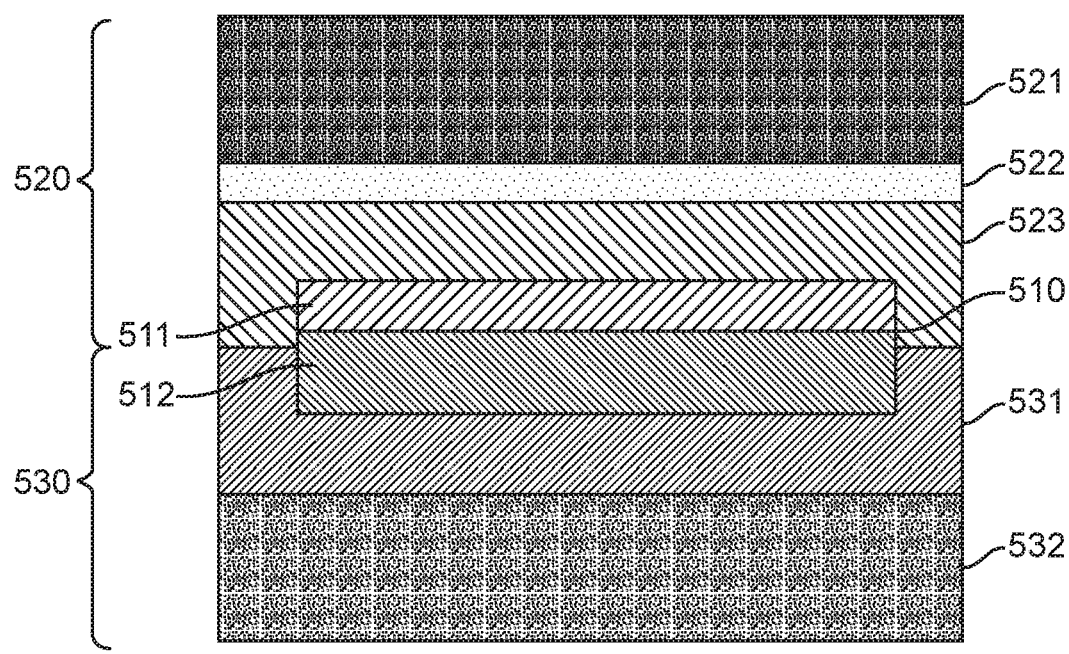
FIG. 5A shows cross section of an edible ornamental indicia carrier in accordance with some embodiments.

FIG. 5A shows an edible ornamental indicia carrier. The ornamental indicia carrier comprises a top laminate 520 and a bottom laminate 530 that encapsulate the ornamental indicia layer 510. Further, the top laminate 520 comprises a conformable film layer 522 having a removable protector layer 521 that is fully or partially contiguous over one surface thereof and a pressure sensitive adhesive layer 523 over the second surface thereof.

Ornamental indicia layer 510 comprises edible colorant layer 511 that is fully or partially contiguous over one surface of the edible carrier layer 512. Bottom laminate 530 comprises of a pressure sensitive adhesive layer 531 and a removable protective layer 532 over one surface. The ornamental indicia carrier is constructed such that the edible colorant layer 511 is facing the adhesive layer 523 of the top laminate and is fully or partially visible through the removable protective layer 521 and the second surface of the edible carrier layer 512 that is free of edible colorants is facing the adhesive layer 531 of the bottom laminate 530. Further, the top laminate 520 and bottom laminate 530 extend beyond the edge of the ornamental indicia layer 510 on all sides to fully encapsulate the indicia layer 510.

In some embodiments, second removable protective layer 532 is a silicone coated release paper. The removable protector may be divided into two or more pieces. At least one of the protector pieces can be significantly larger than the other or others and covers a major proportion of the adhesive layer. The stripping load of the ornamental indicia carrier from the first removable protective layer 521 can be equal to or greater than that of the second removable protective layer 532 from the second adhesive layer 531 to decrease peeling of the ornamental indicia carrier from the first removable protective layer before the second removable protective layer can be removed.

In some embodiments, second removable protective layer 532 is a bleached Kraft paper with silicone coated on one or both sides. In some embodiments, second removable protective layer 532 has thickness from 100 to 200 µm, and preferably 80 to 150 µm, for example 90 µm.

In some embodiments, ornamental indicia layer 510 comprises components that comply with FDA and most international regulations concerning its use in contact with food articles or skin. The ornamental indicia layer 510 can be made of edible components that are used in food and confectionery products.

In some embodiments, Edible colorant layer 511 comprises inks with components classified as direct or indirect food additives and listed under FDA's Drug Master File. In some embodiments, edible colorant layer 511 comprises inks designed for jet printing onto food inserts. In some embodiments, edible colorant layer 511 includes Colorcon NT36 IJ sold by Colorcon, Harleysville, Pa.; or Edible ink refills and cartridges sold by Icinginks, Santa Maria, Calif.

In some embodiments, edible carrier layer 512 comprises components that complies with FDA and most international regulations concerning its use in contact with food articles or skin. In some embodiments, edible carrier layer 512 comprises components that are food based and edible. This layer can be designed to receive the edible colorant layer 511 and provide a good resolution vibrant image. Further, this layer may have sufficient integrity to be imprinted using continuous processes such as inkjet, flexographic or offset processes and can be cut to desired shapes and sizes without any deterioration. In some embodiments, edible carrier layer 512 is has a thickness from 100 to 200 μm, and preferably 80 to 150 μm, for example 150 μm. In some embodiments, edible carrier layer 512 includes Edible Wafer Paper sold by Oasis Supply on Amazon.com; or Chocolate Transfer Sheets sold by Inedibles.com.

Figure 5B:
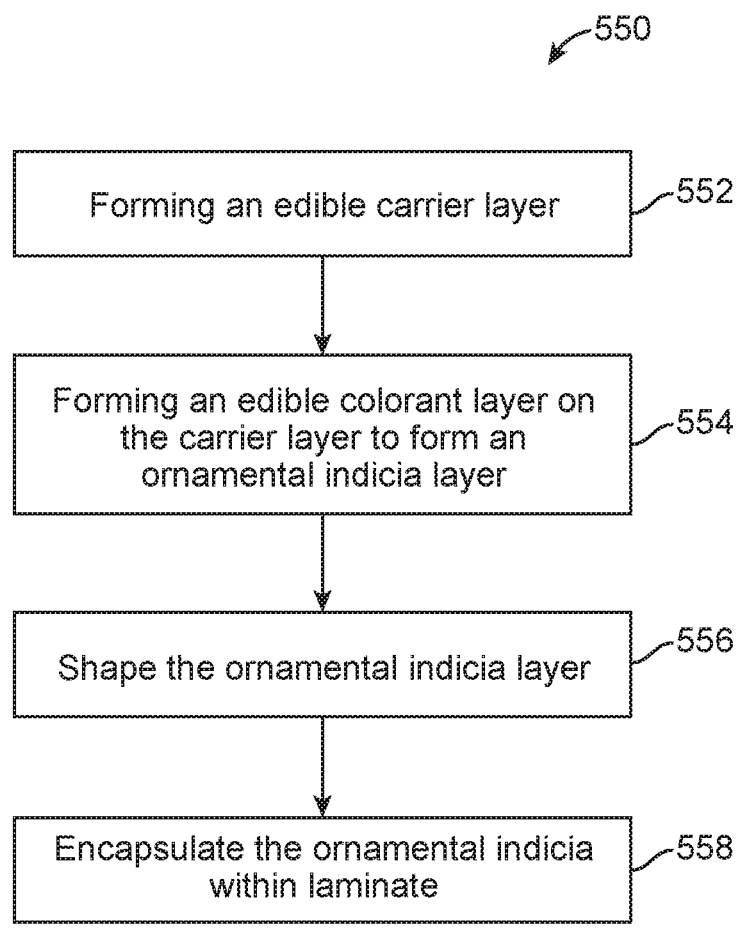
FIG. 5B shows a method of fabricating the surface printed ornamental indicia carrier of FIG. 5A, in accordance with some embodiments.

FIG. 5B shows a method 550 of fabricating an edible ornamental indicial carrier, such as that shown and described with respect to FIG. 5A. At block 552 and edible carrier layer is formed. The edible carrier layer may be formed from components that comply with FDA or other regulations concerning its use in contact with food articles or skin and may be formed from components that are food based or otherwise edible. The edible carrier layer may be configured to receive in edible colorant.

At block 554 and edible colorant layer is formed on the edible carrier layer to form in ornamental indicia layer. The edible colorant layer may be formed from inks made with components classified as direct or indirect food additives, such as those listed under FDA's Drug Master File. The edible colorant layer may be formed by inkjet printing of edible inks onto the edible carrier layer. In some embodiments, may include Colorcon NT36 IJ sold by Colorcon, Harleysville, Pa. or Edible ink sold by Icinginks, Santa Maria, Calif.

At block 556 the ornamental indicia layer is shaped. In some embodiments the ornamental indicia layer is diecut with a die shaped according to a desired final shape of the ornamental indicia layer. In some embodiments a CNC router is controlled to cut the ornamental indicia layer according to a desired final shape of the ornamental indicia layer.

At block 558 the ornamental indicia layer is encapsulated within a laminate. In some embodiments, one or more laminate layers are formed around the ornamental indicia layer in order to encapsulate the ornamental indicia layer within the laminate layer or layers. In some embodiments, a laminate layer includes an adhesive layer and a removable protective layer over the laminate layer. A first surface of the laminate layer corresponding to the surface of the adhesive layer is applied to a first surface of the ornamental indicia layer and a removable protective layer is applied to a second surface of the adhesive layer. In some embodiments, a laminate layer may include a conformable film layer between an adhesive layer on a first surface and a removable protective layer on a second surface.

In some embodiments, a first laminate layer, such as a bottom laminate layer, including both an adhesive layer and a removable protective layer is applied to a first surface of the ornamental indicia layer, such as a surface corresponding to the edible carrier layer and a second laminate layer such as a top laminate layer may be applied to a second surface of the ornamental indicia layer, such as a surface corresponding to an edible colorant layer.

In some embodiments a cavity may be formed within an adhesive layer of a laminate layer. The cavity may be shaped according to a shape of the ornamental indicia layer. In some embodiments, the laminate layers are sized and shaped such that they extend beyond and around the perimeter or the entire perimeter of the ornamental indicia layer such that portions of an adhesive layer of a bottom laminate layer are adhered to both the ornamental indicia layer and an adhesive layer of a top laminate layer, while the adhesive layer of the top laminate layer it adheres to both a surface of the ornamental indicia layer and the adhesive layer of the bottom line layer, in order to encapsulate the ornamental indicia layer.

In some embodiments, a method of manufacture of the ornamental indicia carrier which comprises the steps of: applying the edible colorant layer 511 to a surface of the edible carrier layer 512 one or more of as printing, spraying or brushing to provide the ornamental indicia layer 510; cutting the ornamental indicia layer 510 to desired size and shape; inserting the cut ornamental indicia layer 510 between two continuous webs of the top laminate layer 520 and bottom laminate layer 530; applying pressure to securely adhere the three layers to each other; and cutting the laminated ornamental indicia carrier to shape and size such that the top laminate 520 and bottom laminate 530 extend beyond the edge of the ornamental indicia layer 510 on all sides to fully encapsulate the indicia layer 510.

In some embodiments, the conformable film layer 522 may be formed from polyurethane or polyolefin films that are attached to removable paper or polyester film protective layer 521 and help in handling the thin conformable film layer. In some embodiments, the conformable film layer 522 is sufficiently clear to see through to the ornamental indicia layer 510. In some embodiments, the conformable film layer 522 complies with FDA and most international regulations concerning its use in contact with food articles or skin. In some embodiments, conformable film layer 522 has thickness from 10 to 100 μm, and preferably 20 to 50 μm, for example 20 μm, 30 μm and 50 μm. In some embodiments, conformable film layer 522 with or without the protective layer 521 includes—3M Product 9832F (formerly MSX-6362) sold by 3M Medical Specialties, St. Paul, Minn.; or MBK 3820 and MBK 3202 sold by MBK Tape Solutions, Chatsworth, Calif.

In some embodiments, the removable protective layer 521 has thickness from 50 to 150 μm, and preferably 80 to 130 μm. In some embodiments, the purpose of the removable protective layer 521 is to assist in handling of the conformable film layer 522. Certain choices for the conformable film layer, especially polyolefin films with thickness from 30 to 50 μm may not require a removable protective layer.

In some embodiments, the pressure sensitive adhesive layers 523, 531 may preferably be formed from an adhesive which is configured for contact with the skin. The pressure sensitive adhesive can be a high tack synthetic rubber-based transfer adhesive designed for medical device applications and is approved for use on skin. In some embodiments, the pressure sensitive adhesive layer 523 is sufficiently clear to see through to the ornamental indicia layer 510. In some embodiments, the pressure sensitive adhesive layer 531 is sufficiently clear to see through to the dental appliance surface. In some embodiments, the pressure sensitive adhesive layer 523 & 531 has thickness from 50 to 200 μm, and preferably 80 to 150 μm, for example 50 μm and 110 μm.

In some embodiments, pressure sensitive adhesive layer 523 includes—3M Product 1504XL sold by 3M Medical Specialties, St. Paul, Minn.; or Polyken 3426A sold by Berry Plastics, Franklin, Mass.

Figure 6:
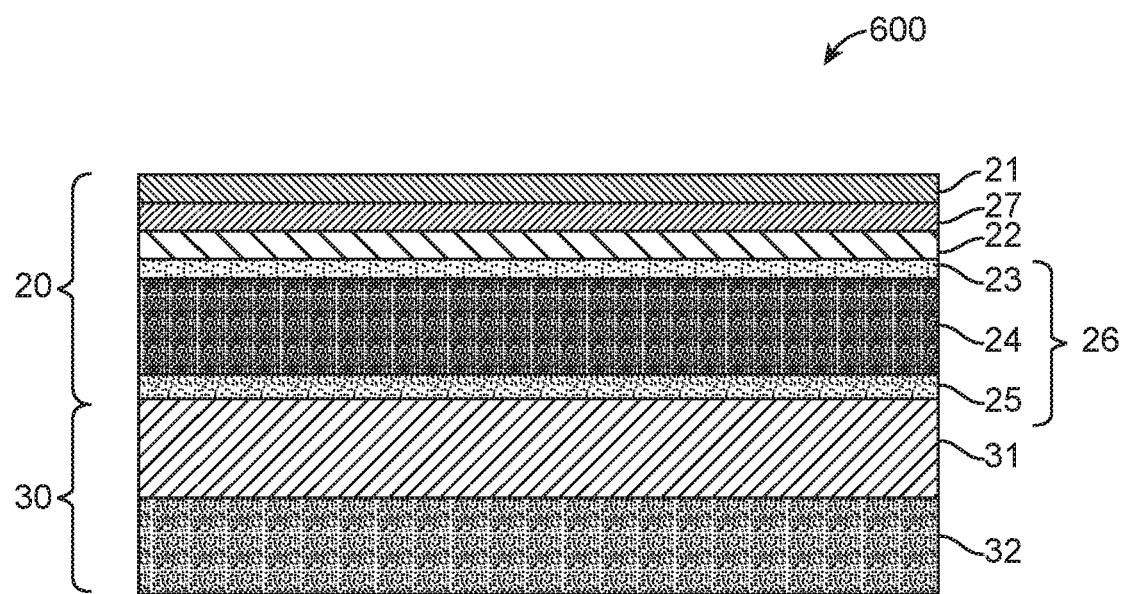
FIG. 6 shows a cross section of an ornamental indicia carrier including a plurality of indicial layers, in accordance with some embodiments.

FIG. 6 shows a surface printed ornamental indicia carrier 600 comprising a top print laminate 20 layer including first and second indicia layers 22, 27 and an adhesive laminate 30. The top print laminate 20 comprises an oriented print layer 26. The oriented print layer 26 comprises a core layer

24, a first adhesion layer 23 and a second adhesion layer 25. The first adhesion layer 23 extends along the core layer 24 and can be fully contiguous over a surface of the core layer. The second adhesion layer 25 extends along a second surface of the core layer 24. In some embodiments, the exposed surface of the first adhesion layer is further treated to enhance print adhesion. The treated surface can then be decorated by first indicia layer 22, such as an ink layer printed using UV inkjet printing. The ink layer can be fully or partially contiguous across the surface of the top print laminate.

The ornamental indicia carrier 600 may include a second indicia layer 27. The second indicia layer may include additional features such as glow-in-the-dark material, glitter, additional paints, and material to reduce reflectivity of the external surface of the ornamental indicia carrier 600. In some embodiments, the second indicia layer may be a second printed layer, such as a second ink layer. A second printed layer may include printed ink the glows in the dark after being stimulated by ambient light, may include glitter or other fine particles that reflect light, or may include materials that reduce the reflectivity of the layers of the aligner. In some embodiments, the second indicia layer is a second film layer wherein the film of the second film layer comprises glow-in-the-dark properties, is embedded with reflective material to give a glitter effect, or includes surface treatment to reduce reflections and shine.

A glow-in-the-dark effect may be provided for as either a film or through ink, as discussed above. In either embodiment, the glow-in-the-dark material may include phosphors that emit visible light after being energized. For example, the phosphors may be energized using ambient light or through the use of a flashlight, an LED light on a phone, or other light stimulation. After being stimulated, the phosphors of the glow-in-the-dark material are energized and may emit visible light.

A glitter effect may also be provided for as either a film or through ink, as discussed above. In film form the glitter effect may be provided by a film comprising reflective particles embedded within the film. The embedded particles may be distributed within the film at various locations and having surfaces oriented in different arrangements. In some embodiments glitter effect may be provided by particles having surfaces oriented in the same direction. In some embodiments, reflective particles may be held in suspension within a clear or transparent medium that is then painted or printed onto the carrier and then cured.

In some embodiments, the first indicia layer and the second indicia layer may include different inks or paints. For example, inks or paints of a first indicia layer may be incompatible with inks or paints of a second indicia layer. In such embodiments, inks of the first indicia layer may be applied and cured prior to application and curing of the second indicia layer on top of the first indicia layer.

In some embodiments, the first and/or second indicia layer may include reflective material. For example, in indicia layer may be formed from a film including a continuous or substantially continuous reflective surface. Using such a reflective surface may provide a mirrorlike finish on the ornamental indicia carrier. For example, in some embodiments a gold or silver colored reflective film may provide for a corresponding gold, silver, or metallic mirrored surface.

In some embodiments, the indicia carrier may include a surface that reduces reflectivity or glare. For example, an outer layer such as a varnish layer 21 or an outer surface of an ink or other indicia layer 22 may be treated to provide a matte or other finish that reduces the surface reflections of the surface. For example, a rubbing compound or other volatile compound may be applied to the outer surface in order to create a matte finish. In some embodiments, an outer layer may comprise a film or material with surface or material properties that provide a matte finish. In some embodiments an ink or overspray may be provided on an external surface of the indicia carrier to reduce the reflectivity of the surface.

In some embodiments, and indicia layer such as an ink layer 22 may include colors, such as those provided by inks or other pigments, that change based on their temperature. For example, the indicia layer may be a first color or clear when the temperature is at or below a normal body temperature and may be a second color when the temperature is above a normal body temperature. For example, an ink or pigment may be colorless below 100° F. and may turn red above 100° F. In some embodiments another color transition threshold may be set, for example 99° F. In some embodiments the color may change from a first color such as green or white at a first temperature and to a second color such as red or blue and a second temperature. In some embodiments, the color or translucency of the material may change gradually based on temperature. For example, in indicia layer may be colorless below 96° F., transition from colorless to red between 96° F. and 100° F., in be red above 100° F. Such color change may be implemented using thermo chromatic inks.

In some embodiments, and indicia layer such as an ink layer 22 may include colors, such as those provided by inks or other pigments, that change based on the intensity of light on the indicia layer. For example, the indicia layer may be a first color or clear when the light intensity is at or below a first threshold and may be a second color or shade when the light intensity is above the first threshold. In some embodiments, the shade or translucency of the material may change gradually based on light intensity. For example, in indicia layer may be a first shade or clear below a first threshold, transition from the first shade to a second shade or from clear to opaque at a second light intensity threshold, in be the second shade or opaque above the second light intensity threshold. Such color change may be implemented using photo chromatic inks. In some embodiments, the indicia layer may include silver chloride or other silver halide embedded or held in suspension within the ink.

In some embodiments, the ink layer may include indicia indicative of customized logos or names an order to show support for or provide advertising for a particular company, sports team, or cause. In some embodiments, such indicia may be visible external to the wearer's mouth, such as on the upper incisors and canines.

In some embodiments the indicia may be placed in a location not visible by others when a patient is wearing the indicia. For example, it may be beneficial to obscure the indicia when the indicia contains identifying information such as a barcode a 2D barcode a QR barcode or other images and information such as trademarks identifying the source of the indicia or aligners to which they are attached.

In some embodiments, a clear overprint varnish (OPV) may be applied over the first and second indicia layers to encapsulate the image areas on the surface. The clear OPV can be fully or partially contiguous across the image area so as to encapsulate the UV ink, for example so as to fully encapsulate the UV ink. The clear OPV can be applied by one or more techniques such as direct coating, transfer coating or printing. In some embodiments the OPV layer is printed, for example by in-line UV inkjet printing. In some embodiments, the OPV layer is present only in the areas where the ink layer is present. The bottom laminate 30 comprises of a pressure sensitive adhesive layer 31 and a removable protective liner 32 extending over a surface of the pressure sensitive adhesive layer 31. The ornamental indicia carrier can be constructed such that the adhesion layer 25 of the top print laminate is facing and in contact with the pressure sensitive adhesive layer 31 of the bottom adhesive laminate. In some embodiments, the top laminate 20 and bottom laminate 30 are fully contiguous across their interface.

Figure 7:
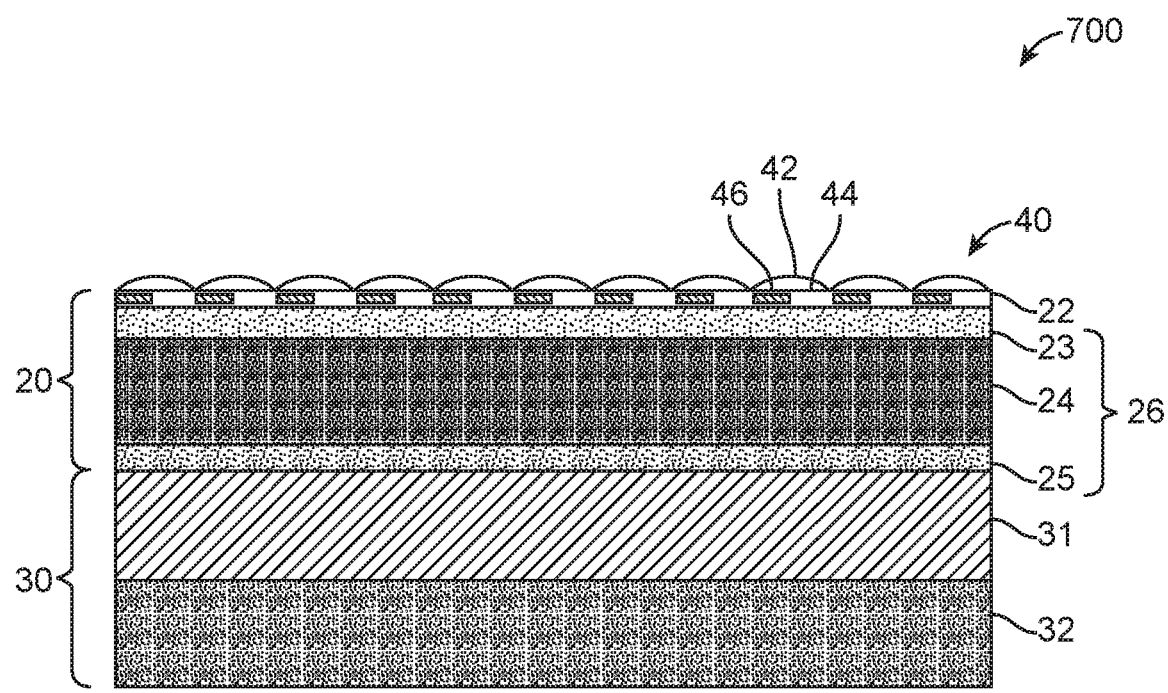
FIG. 7 shows a cross section of an ornamental indicia carrier including a lenticular structure, in accordance with some embodiments.

FIG. 7 shows a surface printed ornamental indicia carrier 700 comprising a top print laminate 20 layer that includes a lenticular print layer, and an adhesive laminate 30. The top print laminate 20 comprises an oriented print layer 26. The oriented print layer 26 comprises a core layer 24, a first adhesion layer 23 and a second adhesion layer 25. The first adhesion layer 23 extends along the core layer 24 and can be fully contiguous over a surface of the core layer. The second adhesion layer 25 extends along a second surface of the core layer 24. In some embodiments, the exposed surface of the first adhesion layer is further treated to enhance print adhesion. The treated surface can then be decorated by indicia layer 22, such as an ink layer printed using UV inkjet printing. The ink layer can be fully or partially contiguous across the surface of the top print laminate.

The indicia layer 22 may be part of the lenticular layer 40. The lenticular layer may comprise a plurality of lenticular lenses 42 formed over the top of the indicia layer 22. The indicia layer 22 may be comprised of two images printed in alternating strips 44, 46. Each lens 42 is formed over a pair of alternating strips 44, 46 such that a first strip 44 representing a portion of a first image is formed on a first half of a lenticular lens 42 while a second strip 46 representing a portion of a second image is formed on a second half of a lenticular lens 42. A linear array of several lenses may be formed over alternating pairs of strips 44, 46 of the two images. The lenses in combination with the strips of the images allow for the two images to be displayed to a user each being individually viewable from a different angle or range of angles.

The lenticular lenses 42 may be shaped based on the curvature of the surface of the object that are to be applied to so that the lenticular layer displays the two images when the ornamental indicial is applied to a curved surface, such as the curved surface of a orthodontic aligner.

In some embodiments, the exposed surface of the first adhesion layer is treated to enhance print adhesion. For example, the surface treatment may comprise one or more methods such as corona, flame or plasma treatment techniques. The treated surface may then be decorated by an ink layer printed using UV inkjet printing. The ink layer can further comprise one or more specific colored inks and an optional white ink to provide opacity in order to enhance color density. The ink layer can be fully or partially contiguous across the surface of the top print laminate. In some embodiments, the bottom laminate 30 comprises a pressure sensitive adhesive layer 31 and a removable protective liner 32 over a surface of the pressure sensitive adhesive. In some embodiments, the ornamental indicia carrier is constructed such that the adhesion layer 25 of the top print laminate is facing and in contact with the pressure sensitive adhesive layer 31 of the bottom adhesive laminate. In some embodiments, the top laminate 20 and adhesive laminate 30 are fully contiguous across their interface.

Figure 8A:
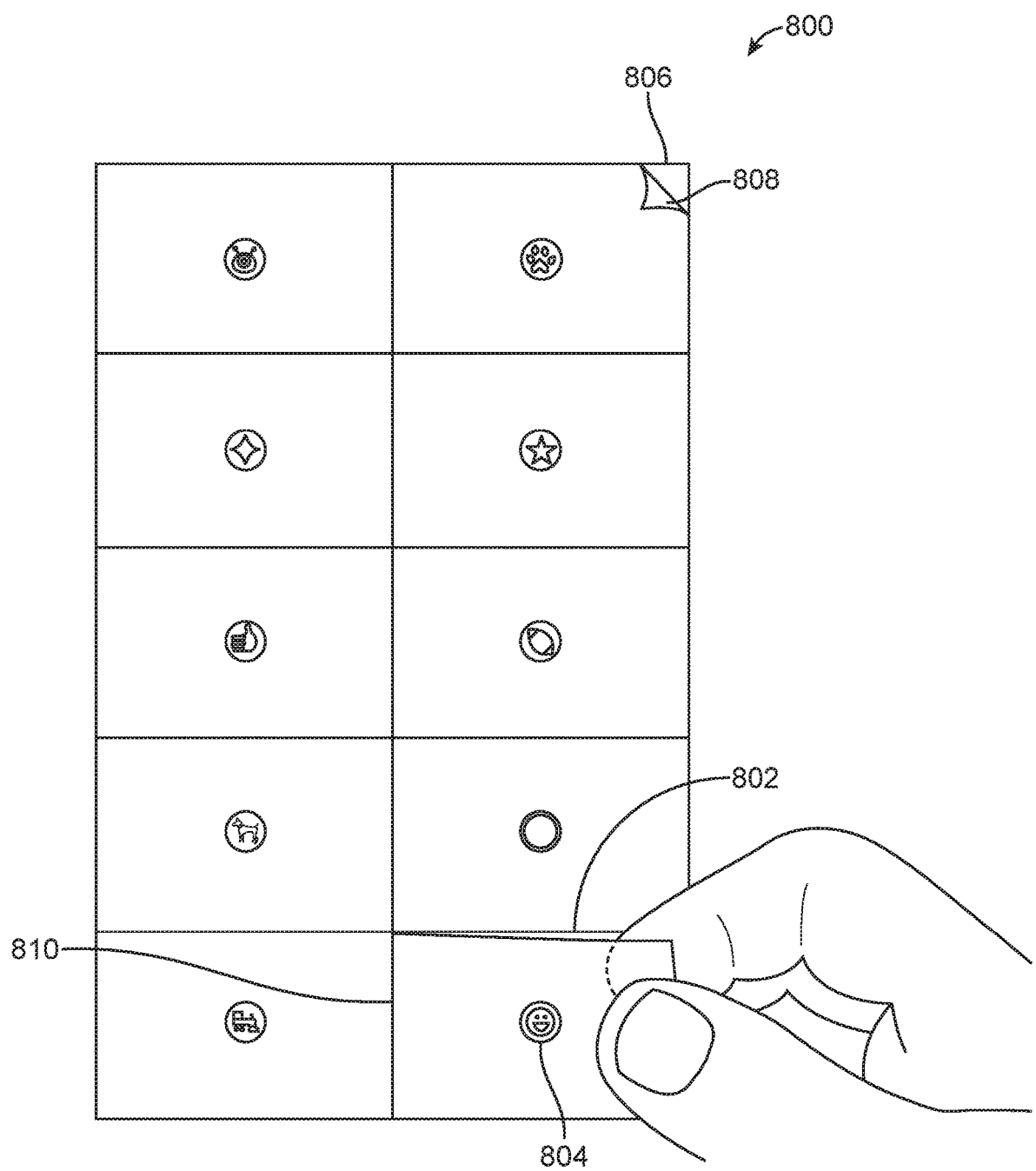
FIGS. 8A-8D show aspects of a method of applying an ornamental indicia carrier to an object, in accordance with some embodiments.

FIGS. 8A-8D depicts steps of a method for attaching an ornamental indicia carrier to an object such as an orthodontic aligner. FIG. 8A shows a sheet of ornamental indicia 800. The sheet 800 includes 12 ornamental indicia carriers 802. In the embodiment shown in FIG. 8A the ornamental indicia carriers include a top laminate 808 a bottom laminate 806 and in ornamental indicia 804 therebetween. The ornamental indicia 804 may include a core layer, one or more adhesion layers, one or more ink layers, a lenticular layer, and a varnish layer, as described herein. In some embodiments, the ornamental indicia 804 may also include one or more edible colorant layers and an edible carrier layer, as described herein. In some embodiments, the indicia carrier 802 may be any of the indicia carrier shown and described herein. As shown in FIG. 8A, at a first step of the application process a first of the indicia carriers 802 is separated from the sheet of ornamental indicia 800. In some embodiments, the top laminate layer 808, bottom laminate layer 806, and the indicia 804 are separated together from the sheet 800 and then the top laminate layer, the indicia 804, and a pressure sensitive adhesive layer are separated from a removable protective layer that covers the pressure sensitive adhesive layer. In some embodiments, the top laminate layer 808, the indicia 804, and a pressure sensitive adhesive layer are separated together from the sheet 800 and a removable protective layer that covers the pressure sensitive adhesive layer together, for example as a single operation. In some embodiments, each indicia carrier 802 is separated from each other indicia carrier 802 by a score mark or perforations 810. The perforations may pass through one or more of the top laminate layer and the bottom laminate layer. In some embodiments, the bottom laminate layer is an adhesive laminate layer. In some embodiments, the top laminate layer includes a print laminate layer and a top laminate layer such as top laminate layer 502.

Figure 8B:
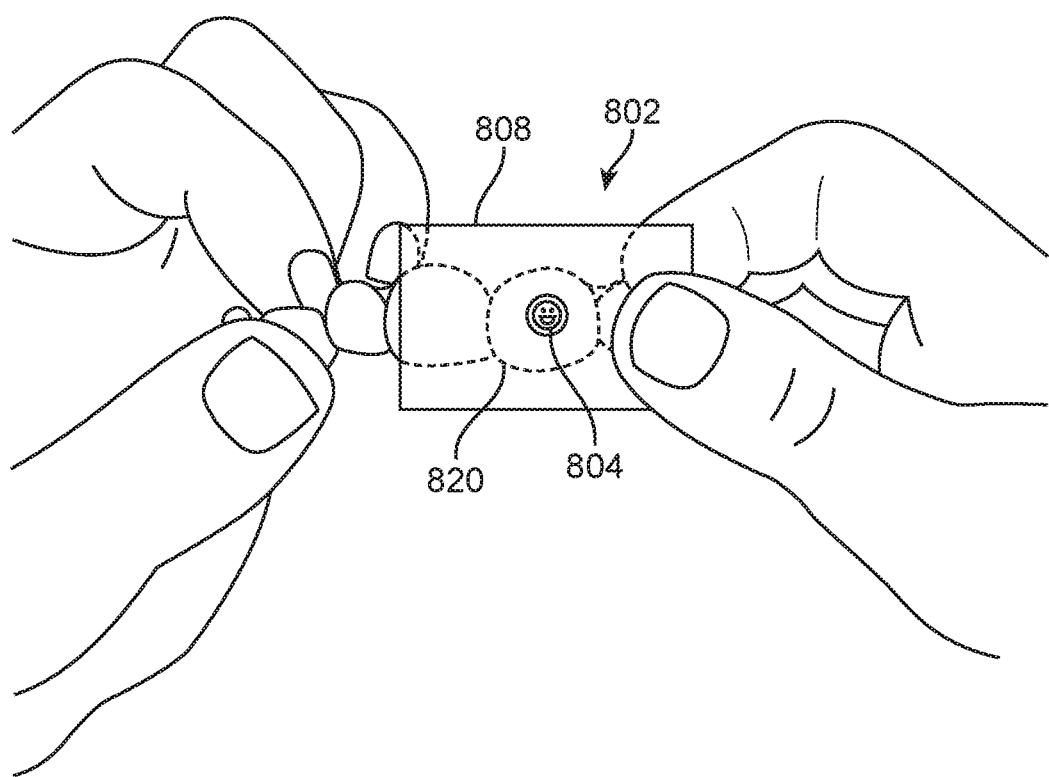

FIG. 8B shows another step in a method 800 of attaching and indicia 804 and object such as an aligner 820. In FIG. 8B the indicia is aligned on a tooth receiving cavity of the aligner 820. The indicia may be placed between the occlusal and gingival edges of an incisal or canine tooth receiving cavity of the aligner 820.

Figure 8C:
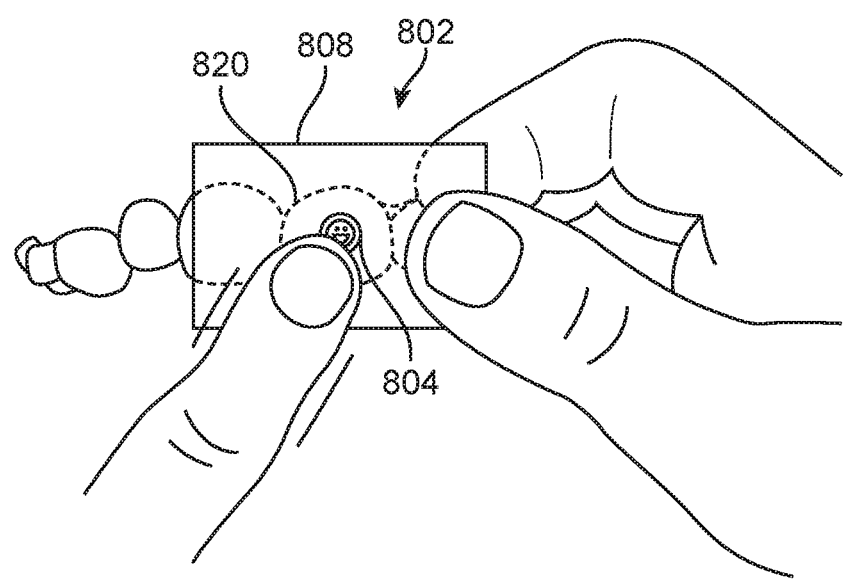

FIG. 8C shows a step of adhering the indicia 804 the aligner 820. As shown in FIG. 8C, the top laminate 808 and/or the indicia 804 is pressed against the tooth receiving cavity of the aligner 822 activate the pressure sensitive adhesive and cause the indicia 804 to adhere to the aligner 820.

Figure 8D:
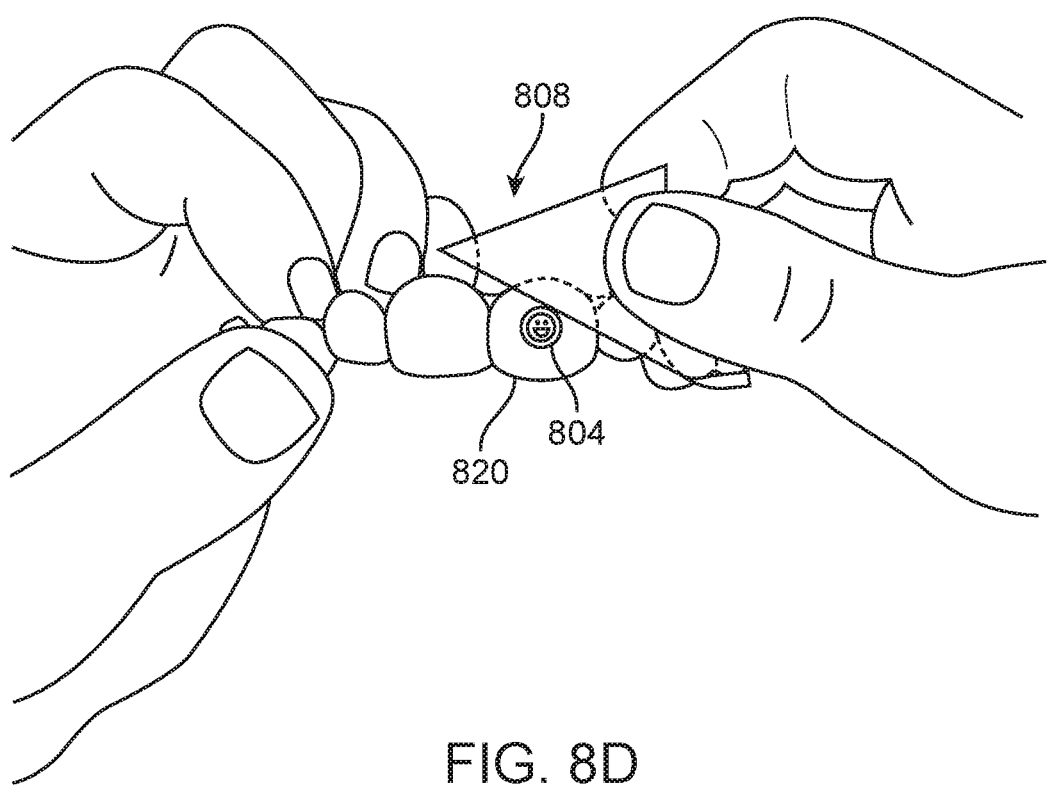

FIG. 8D shows a step of removing the top laminate layer 808. After the indicia 804 is securely adhered to the aligner 820 the top laminate layer may be slowly peeled away from the indicia 804. This uncovers the indicia 804 while leaving it adhered to the aligner 820.

In some embodiments, a method of attaching the ornamental indicia carrier to an object to be decorated such as a dental appliance comprises one or more of the following steps: removing a portion of the removable protective layer 32 to expose the pressure sensitive adhesive layer 31; affixing the ornamental indicia carrier to a location such as a predetermined location on the dental appliance; removing the remaining portions of the removable protective layer 32 to expose the pressure sensitive adhesive layer 31; and affixing one or more portions of the ornamental indicia carrier to the dental appliance by pressing the ornamental indicia carrier toward the dental appliance.

In some embodiments, a method of attaching the ornamental indicia carrier to an object such as a dental appliance comprises: removing a portion of the second protective layer 532 to expose the pressure sensitive adhesive layer 531; affixing the ornamental indicia carrier to a predetermined location on the dental appliance; removing the remaining portions of the second protective layer 532 to fully expose the pressure sensitive adhesive layer 531 and affixing more portions of the ornamental indicia carrier to the dental appliance; and removing the first protective layer 521 to expose the conformable film layer 522 and pressing down on to securely affix the ornamental indicia carrier to the dental appliance.

Figure 9:
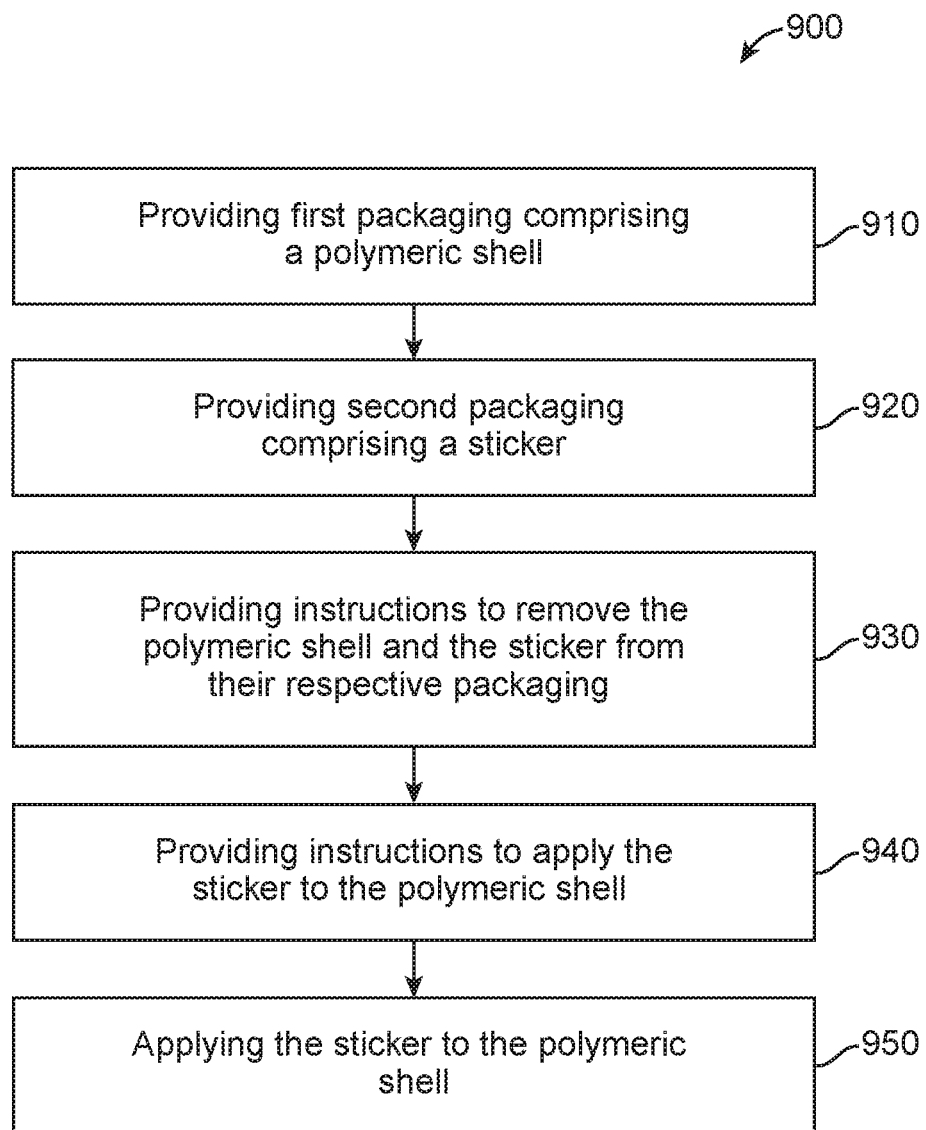
FIG. 9 shows a method of applying an ornamental indicia carrier to an object, in accordance with some embodiments.

FIG. 9 depicts a method 900 of applying a applying an ornamental indicia to an object. At block 910 a first packaging comprising a polymeric shell is provided. The polymeric shell may be in orthodontic aligner comprising a plurality of tooth receiving cavity shaped to receive and resiliently reposition a subject's teeth from a first arrangement towards a second arrangement. The first packaging may be provided to a subject such as a person receiving orthodontic treatment. The first packaging may also comprise a plurality of polymeric shells.

At block 920 a second packaging comprising a sticker, such as an ornamental indicia, is provided. The sticker, such as an ornamental indicia, may include a plurality of layers. The sticker may include a first adhesive layer configured to be adhered to the polymeric shell, a second adhesive layer adhered over the first adhesive layer. The second adhesive layer may include a pressure sensitive adhesive layer. In some embodiments the first adhesive layer may include a pressure sensitive adhesive. In some embodiments, a colorant may be encapsulated between the first adhesive layer and the pressure sensitive adhesive layer of the second adhesive layer. In some embodiments the sticker such as an ornamental indicia may include any of the ornamental indicia described herein and may include any combination of layers of ornamental indicia described herein.

At block 930 instructions are provided to remove the polymeric shell from the first packaging and to remove the sticker from the second packaging. The instructions may include details regarding the use and handling of the polymeric shell and the sticker.

At block 940 instructions are provided to apply the sticker to the polymeric shell. The instructions may include details regarding the use and handling of the sticker in the polymeric shell during application of sticker to the polymeric shell. The instructions may also include details regarding alignment of the sticker with the polymeric shell, such as instructions as to appropriate locations for application of the sticker to the polymeric shell. The instructions may include the steps shown in FIGS. 8A-D.

At block 950 the sticker or other ornamental indicia is applied to the polymeric shell. In some embodiments, applying the stickers or other ornamental indicia to the polymeric shell may follow the process depicted in FIGS. 8A-D. Applying the stickers may include removing a selected indicia from a sheet containing a plurality of indicia, removing a cover layer over a layer pressure sensitive adhesive, arranging the indicia relative to the orthodontic shell in order to determine the application location of the indicia, applying pressure to the sticker and the orthodontic shell to adhere the sticker to the orthodontic shell, and removing a film layer from the ornamental indicia after hearing the ornamental indicia to the orthodontic appliance.

Figure 10:
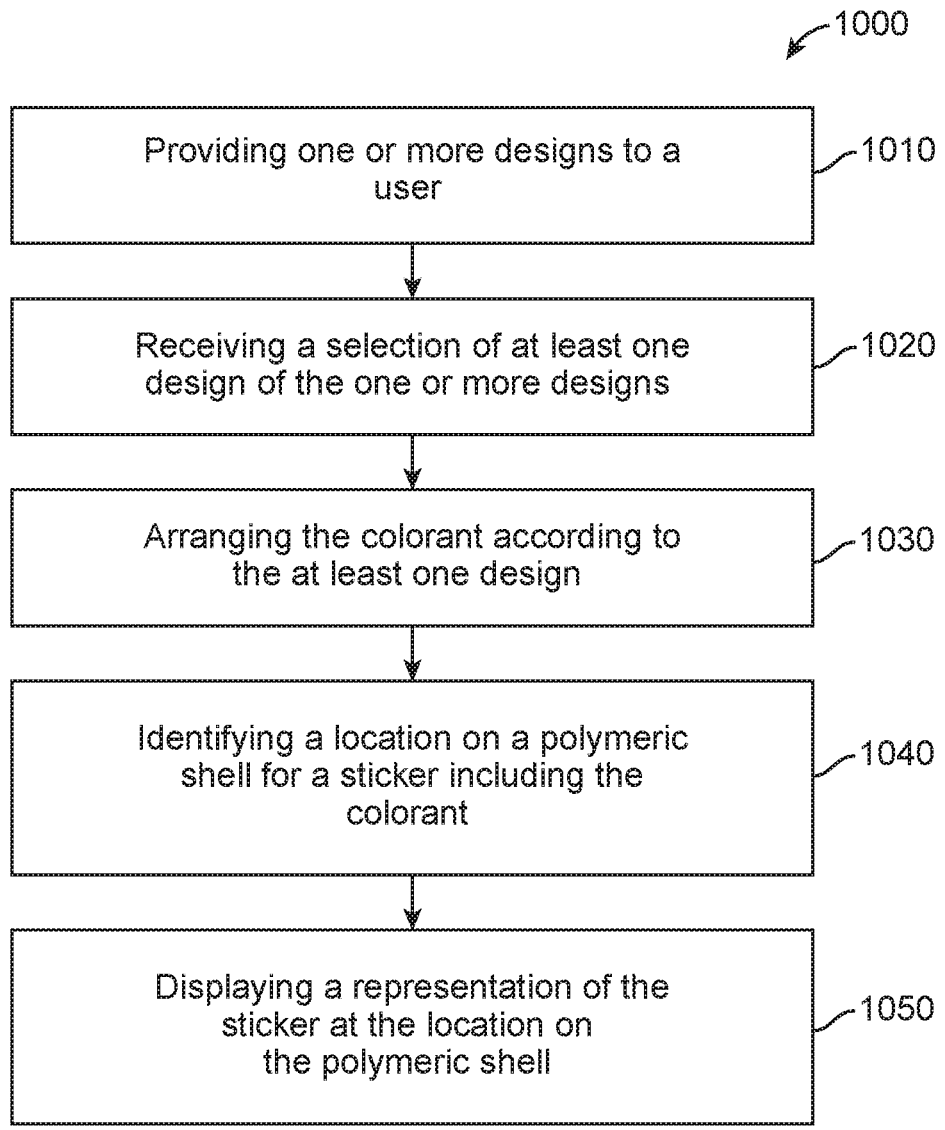
FIG. 10 shows a method of designing an ornamental indicia carrier, in accordance with some embodiments.

FIG. 10 depicts a method 1000 of designing an ornamental indicia for application to an object. At block 1010 one or more designs for an ornamental indicia may be provided to a user. In some embodiments the one or more designs are provided to a user on a computing device associated with the user. In some embodiments, one or more designs may be provided via an advertisement including the one or more designs.

At block 1020 a selection of at least one of the one or more designs is received. In some embodiments the selection is received from a user. In some embodiments the selection may be remotely received from a user. In some embodiments, the selection may be received in response to the advertisement.

At block 1030 colorant is arranged according to at least one of the one or more designs. In some embodiments, the colorant is arranged according to the selected design. In some embodiments, arranging the colorant may include fabrication of an ornamental indicia as discussed herein, for example with respect to at least FIGS. 2-7.

At block 1040 a location on an object such as a polymeric shell for a sticker including the colorant is identified. In some embodiments the location may be a buccal surface of a tooth receiving cavity of the orthodontic shell. In some embodiments the location includes a buccal facing buccal surface of a tooth receiving cavity for receiving and resiliently reposition a canine or an incisor.

At block 1050 a representation of the sticker at the location on the polymeric shell is displayed. For example, FIG. 1 can depict the display of an polymeric shell with a sticker. In some embodiments, a digital representation of the sticker at the location on the polymeric shell is displayed. In some embodiments, the digital representation of the sticker is displayed on a digital representation of an orthodontic shell appliance. In some embodiments, the digital representation of the sticker is displayed on an orthodontic shell appliance applied to an image of the patient's face and teeth.

Figure 11:
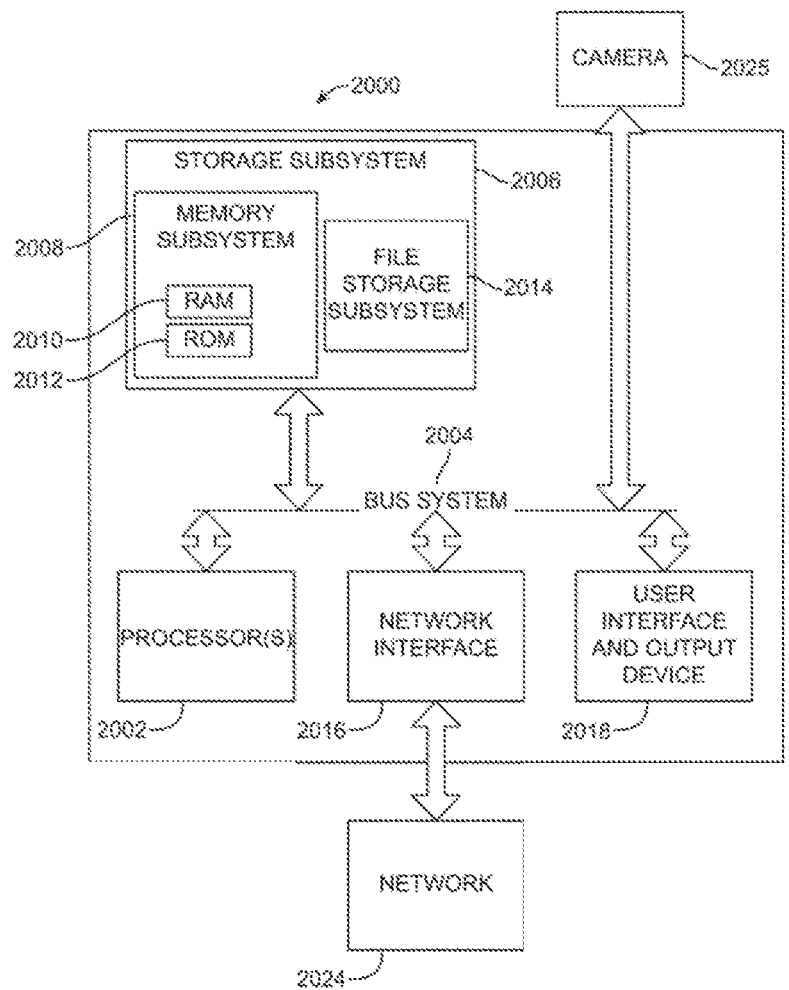
FIG. 11 shows a computing system, in accordance with some embodiments.

FIG. 11 is a simplified block diagram of a data processing system 2000, such as a computing device, that may be used in executing methods and processes described herein. The data processing system 2000 may include at least one processor 2002 that communicates with one or more peripheral devices via bus subsystem 2004. These peripheral devices typically include a storage subsystem 2006 (memory subsystem 2008 and file storage subsystem 2014), a set of user interface input and output devices 2018, and an interface to outside networks 2016. This interface is shown schematically as "Network Interface" block 2016, and is coupled to corresponding interface devices in other data processing systems via communication network interface 2024. Data processing system 2000 can include, for example, one or more computers, such as a personal computer, workstation, mainframe, laptop, and the like.

The user interface input devices 2018 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 2006 maintains the basic required programming, including computer readable media having instructions (e.g., operating instructions, etc.), and data constructs. The program modules discussed herein are typically stored in storage subsystem 2006. Storage subsystem 2006 typically includes memory subsystem 2008 and file storage subsystem 2014. Memory subsystem 2008 typically includes a number of memories (e.g., RAM 2010, ROM 2012, etc.) including computer readable memory for storage of fixed instructions, instructions and data during program execution, basic input/output system, etc. File storage subsystem 2014 provides persistent (non-volatile) storage for program and data files, and can include one or more removable or fixed drives or media, hard disk, floppy disk, CD-ROM, DVD, optical drives, and the like. One or more of the storage systems, drives, etc., may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

The system may communicate via a network interface 2024. The system may be located, for example, at a remote location and receive or transmit data from one or more other data processing systems 2000 via network interface 2024. The camera 2025 may include any image capture device configured to capture still images or movies. The camera 2025 may facilitate capturing various perspectives of a patient's dentition and face, for example to display the patient's face with the polymeric shell and stickers. In some implementations, the camera 2025 may facilitate capture of images at various focal lengths and distances from the patient.

The data processing aspects of the methods described herein can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing blocks can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

The ornamental indicia carrier may be produced to different sizes to fit various types of dental appliances and placed in a bacteria proof pouch, sealed and sterilized by conventional methods including using ethylene oxide or irradiation.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "top", "bottom", "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

Clause 1. An ornamental indicia carrier, comprising: a first print laminate comprising an oriented print layer, the oriented print layer comprising a core layer, a first adhesion layer and a second adhesion layer; a second print laminate connected to the first print laminate, the second print laminate comprising a pressure sensitive adhesive layer; and an ink layer coupled to one or more of the first adhesion layer, the second adhesion layer or the pressure sensitive adhesive layer.

Clause 2. The ornamental indicia carrier of clause 1, wherein the second adhesion layer is contiguous with the pressure sensitive adhesive.

Clause 3. The ornamental indicia carrier of clause 1, further comprising a varnish layer on the ink layer.

Clause 4. The ornamental indicia carrier of clause 1, wherein the ink layer is located between the second adhesion layer and the pressure sensitive adhesive layer.

Clause 5. The ornamental indicia carrier of clause 1, further comprising a lenticular layer.

Clause 6. The ornamental indicia carrier of clause 5, wherein the lenticular layer comprises the ink layer and a lenticular lens layer.

Clause 7. The ornamental indicia carrier of clause 1, wherein the ink layer is a first indicia layer and further comprising a second indicia layer.

Clause 8. The ornamental indicia carrier of clause 7, wherein the second indicia layer is a film layer.

Clause 9. The ornamental indicia carrier of clause 8, wherein the film layer comprises photo sensitive polymer or pigment.

Clause 10. The ornamental indicia carrier of clause 8, wherein the film layer comprises thermo sensitive polymer or pigment.

Clause 11. The ornamental indicia carrier of clause 8, wherein the film layer comprises reflective material.

Clause 12. The ornamental indicia carrier of clause 11, wherein the reflective material is a plurally of reflective material distributed within the film.

Clause 13. The ornamental indicia carrier of clause 11, wherein the reflective material is gold or silver colored.

Clause 14. The ornamental indicia carrier of clause 11, wherein the reflective material provides a mirror finish.

Clause 15. The ornamental indicia carrier of clause 7, wherein the second indicia layer is a second ink layer.

Clause 16. The ornamental indicia carrier of clause 1, wherein the ink layer comprises a glow-in-the-dark material.

Clause 17. The ornamental indicia carrier of clause 8, wherein the film layer comprises a matte finish.

Clause 18. The ornamental indicia carrier of clause 1, wherein an outer surface of the first print laminate film layer comprises a matte finish.

Clause 19. The ornamental indicia carrier of clause 18, wherein a varnish layer provides the matte finish.

Clause 20. A method of manufacturing an ornamental indicia carrier, comprising: treating an exposed surface of an adhesion layer with a corona treatment; applying a UV ink layer to a treated surface of the adhesion layer; inkjet printing a top print laminate; laminating the top print laminate to a bottom adhesive laminate; and cutting the top print laminate and the bottom adhesive laminate.

Clause 21. The method of manufacturing an ornamental indicia carrier of clause 18, wherein, inkjet printing a top print laminate comprises: jetting ink onto the top print laminate; and curing the ink.

Clause 22. The method of manufacturing an ornamental indicia carrier of clause 18, wherein, curing the ink comprises only partially curing the ink, and further comprising: applying an overprint varnish to the partially cured ink; and curing the partially cured ink and the overprint varnish.

Clause 23. The method of manufacturing an ornamental indicia carrier of clause 18, wherein the curing is a UV curing process.

Clause 24. The method of manufacturing an ornamental indicia carrier of clause 17, further comprising: jetting ink onto the top print laminate; and curing the ink.

Clause 25. The method of manufacturing an ornamental indicia carrier of clause 17, further comprising: forming lenticular lens layer on the ink layer.

Clause 26. The method of manufacturing an ornamental indicia carrier of clause 17, wherein the ink comprises photo sensitive polymer or pigment.

Clause 27. The method of manufacturing an ornamental indicia carrier of clause 17, wherein the ink comprises thermo sensitive polymer or pigment.

Clause 28. The method of manufacturing an ornamental indicia carrier of clause 25, wherein the ink comprises a glow-in-the-dark material.

Clause 29. The method of manufacturing an ornamental indicia carrier of clause 17, further comprising applying a film layer to the top print laminate.

Clause 30. The method of manufacturing an ornamental indicia carrier of clause 25, wherein the film layer comprises reflective material.

Clause 31. The method of clause 26, wherein the reflective material is a plurally of reflective material distributed within the film.

Clause 32. The method of clause 26, wherein the reflective material is gold or silver colored.

Clause 33. The method of clause 26, wherein the reflective material provides a mirror finish.

Clause 34. The method of manufacturing an ornamental indicia carrier of clause 25, wherein the film layer comprises photo sensitive polymer or pigment.

Clause 35. The method of manufacturing an ornamental indicia carrier of clause 25, wherein the film layer comprises thermo sensitive polymer or pigment.

Clause 36. The method of manufacturing an ornamental indicia carrier of clause 25, wherein the film comprises a glow-in-the-dark material.

Clause 37. A method of attaching an ornamental indicia carrier to an object, comprising: removing a portion of a removable protective layer to expose a pressure sensitive adhesive layer; and affixing the ornamental indicia carrier to the object.

Clause 38. The method of attaching an ornamental indicia carrier to an object of clause 34, further comprising: activating the pressure sensitive adhesive layer my pressing the ornamental indicia carrier onto the object.

Clause 39. The method of attaching an ornamental indicia carrier to an object of clause 34, further comprising: aligning the ornamental indicial carrier with the object.

Clause 40. The method of attaching an ornamental indicia carrier to an object of clause 36, wherein aligning the ornamental indicial carrier with the object, comprises: aligning the ornamental indicial carrier with a tooth receiving cavity of an orthodontic aligner.

Clause 41. The method of attaching an ornamental indicia carrier to an object of clause 37, wherein the tooth receiving cavity of an orthodontic aligner is an incisal or canine tooth receiving cavity.

Clause 42. An ornamental indicia carrier, comprising: a first adhesive layer; a second adhesive layer; and an edible colorant encapsulated between the first adhesive layer and the second adhesive layer.

Clause 43. A method comprising: applying an edible colorant layer to a surface of an edible carrier layer; cutting an ornamental indicia layer to desired size and shape; and encapsulating the edible colorant layer and the cut ornamental indicia layer between a top laminate layer and a bottom laminate layer.

Clause 44. A dental appliance comprising: a polymeric shell having a plurality of tooth-receiving cavities shaped to receive and resiliently reposition a subject's teeth from a first arrangement toward a second arrangement; a first adhesive layer configured to be adhered to the polymeric shell; a second adhesive layer adhered over the first adhesive layer, the second adhesive layer comprising a pressure sensitive adhesive layer; a colorant encapsulated between the first adhesive layer and the pressure sensitive adhesive layer of the second adhesive layer.

Clause 45. The dental appliance of clause 41, wherein the colorant comprises an edible colorant.

Clause 46. The dental appliance of clause 41, wherein the colorant comprises a biocompatible material.

Clause 47. The dental appliance of clause 41, wherein the colorant is arranged according to a design comprising an ornamental design, a logo, text, advertising material, informational material, or some combination thereof.

Clause 48. The dental appliance of clause 41, wherein the colorant is part of an ink layer.

Clause 49. The dental appliance of clause 41, wherein the colorant comprises a photo sensitive polymer or pigment.

Clause 50. The dental appliance of clause 41, wherein the colorant comprises a thermo sensitive polymer or pigment.

Clause 51. The dental appliance of clause 41, wherein the colorant comprises a reflective material, a glow-in-the-dark material, or some combination thereof.

Clause 52. The dental appliance of clause 41, wherein the colorant provides a reflective finish to the dental appliance.

Clause 53. The dental appliance of clause 41, wherein the first adhesive layer is part of a first print laminate comprising an oriented print layer with a core layer.

Clause 54. The dental appliance of clause 41, further comprising a lenticular layer, wherein the lenticular layer comprises the colorant and a lenticular lens layer.

Clause 55. The dental appliance of clause 41, wherein the dental appliance is one of a series of dental appliance configured to incrementally reposition teeth from an initial position toward a target position.

Clause 56. The dental appliance of clause 41, wherein the dental appliance comprises a multi-layer material having a first polymer layer with a first elastic modulus and a second polymer layer with a second elastic modulus, wherein the second elastic modulus is less than the first elastic modulus.

Clause 57. The dental appliance of clause 41, wherein the dental appliance comprises a multi-layer material having two first polymer layer with a first elastic modulus and a second polymer layer with a second elastic modulus, wherein the second elastic modulus is less than the first elastic modulus and the second polymer layer resides between the two first polymer layers.

Clause 58. The dental appliance of clause 41, wherein the dental appliance comprises a multi-layer material having a first polymer layer with a first elastic modulus and two second polymer layers with a second elastic modulus, wherein the second elastic modulus is less than the first elastic modulus and the first polymer layer resides between the two second polymer layers.

Clause 59. The dental appliance of clause 41, wherein the first adhesive layer and the second adhesive layer are durably adhered to the dental appliance.

Clause 60. The dental appliance of clause 41, wherein the first adhesive layer and the second adhesive layer remain adhered to a desirable level after a 24 hour water immersion test in water at a temperature corresponding to a person's oral cavity.

Clause 61. The dental appliance of clause 41, wherein the first adhesive layer, the second adhesive layer, and the colorant comprise a sticker to be applied onto the dental appliance.

Clause 62. A dental appliance comprising: a polymeric shell having a plurality of tooth-receiving cavities shaped to receive and resiliently reposition a subject's teeth from a first arrangement toward a second arrangement; first adhesion means to adhere to the polymeric shell; second adhesion means disposed over the first adhesion means, the second adhesion means comprising a pressure sensitive adhesive layer; a colorant encapsulated between the first adhesion means and the pressure sensitive adhesive layer of the second adhesion means.

Clause 63. A method comprising: providing a polymeric shell having a plurality of tooth-receiving cavities shaped to receive and resiliently reposition a subject's teeth from a first arrangement toward a second arrangement; providing a sticker comprising: a first adhesive layer configured to be adhered to the polymeric shell; a second adhesive layer adhered over the first adhesive layer, the second adhesive layer comprising a pressure sensitive adhesive layer; a colorant encapsulated between the first adhesive layer and the pressure sensitive adhesive layer of the second adhesive layer; applying the sticker to the polymeric shell.

Clause 64. The method of clause 60, further comprising providing instructions to apply the sticker to the polymeric shell.

Clause 65. The method of clause 60, further comprising providing instructions to a computing device associated with a user to apply the sticker to the polymeric shell.

Clause 66. The method of clause 60, further comprising providing instructions to apply the sticker to the polymeric shell, wherein the instructions specify a particular location on the polymeric shell to apply the sticker.

Clause 67. The method of clause 60, further comprising: providing first packaging comprising the polymeric shell; providing second packaging comprising the sticker; providing instructions to remove the polymeric shell from the first packaging and to remove the sticker from the second packaging; providing instructions to apply the sticker to the polymeric shell.

Clause 68. The method of clause 60, further comprising: providing first packaging comprising a plurality of dental appliances, wherein one dental appliance of the plurality of dental appliance comprises the polymeric shell; providing second packaging comprising the sticker; providing instructions to remove the polymeric shell from the first packaging and to remove the sticker from the second packaging.

Clause 69. The method of clause 60, further comprising: providing one or more designs to a user; receiving a selection of at least one design of the one or more designs; arranging the colorant according to the at least one design.

Clause 70. The method of clause 60, further comprising: providing one or more designs to a user on a computing device associated with the user; remotely receiving a selection of at least one design of the one or more designs at the computing device without the user going to a dental office; arranging the colorant according to the at least one design.

Clause 71. The method of clause 60, further comprising: providing, at a computing device associated with a user, an advertisement with one or more designs to the user; receiving, at the computing device, a selection of at least one design of the one or more designs, the selection being in response to the advertisement; arranging the colorant according to the at least one design.

Clause 72. The method of clause 60, further comprising: providing, at a computing device associated with a user, one or more designs to a user; receiving, at the computing device, a selection of at least one design of the one or more designs; identifying, at the computing device, a location of the sticker on the polymeric shell; displaying, at the computing device a representation of the sticker at the location on the polymeric shell.

Clause 73. The method of clause 60, further comprising: providing, at a computing device associated with a user, one or more designs to a user; receiving, at the computing device, a selection of at least one design of the one or more designs; identifying, at the computing device, a location of the sticker on the polymeric shell, wherein the location is chosen to optimize adherence of the sticker to the polymeric shell.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof

What is claimed is:

1. An ornamental indicia carrier, comprising:
a first print laminate comprising an oriented print layer, the oriented print layer comprising a core layer, a first adhesion layer and a second adhesion layer;
a second print laminate connected to the first print laminate, the second print laminate comprising a pressure sensitive adhesive layer; and
an ink layer coupled to one or more of the first adhesion layer, the second adhesion layer or the pressure sensitive adhesive layer.

2. The ornamental indicia carrier of claim 1, wherein the second adhesion layer is contiguous with the pressure sensitive adhesive layer.

3. The ornamental indicia carrier of claim 1, further comprising a varnish layer on the ink layer.

4. The ornamental indicia carrier of claim 1, wherein the ink layer is located between the second adhesion layer and the pressure sensitive adhesive layer.

5. The ornamental indicia carrier of claim 1, further comprising a lenticular layer.

6. The ornamental indicia carrier of claim 5, wherein the lenticular layer comprises the ink layer and a lenticular lens layer.

7. The ornamental indicia carrier of claim 1, wherein the ink layer is a first indicia layer and further comprising a second indicia layer.

8. The ornamental indicia carrier of claim 7, wherein the second indicia layer is a film layer.

9. The ornamental indicia carrier of claim 8, wherein the film layer comprises photo sensitive polymer or pigment.

10. The ornamental indicia carrier of claim 8, wherein the film layer comprises thermo sensitive polymer or pigment.

11. The ornamental indicia carrier of claim 8, wherein the film layer comprises reflective material.

12. The ornamental indicia carrier of claim 11, wherein the reflective material is a plurally of reflective material distributed within the film layer.

13. The ornamental indicia carrier of claim 11, wherein the reflective material is gold or silver colored.

14. The ornamental indicia carrier of claim 11, wherein the reflective material provides a mirror finish.

15. The ornamental indicia carrier of claim 7, wherein the second indicia layer is a second ink layer.

16. The ornamental indicia carrier of claim 1, wherein the ink layer comprises a glow-in-the-dark material.

17. The ornamental indicia carrier of claim 8, wherein the film layer comprises a matte finish.

18. The ornamental indicia carrier of claim 1, wherein an outer surface of the first print laminate comprises a matte finish.

19. The ornamental indicia carrier of claim 18, wherein a varnish layer provides the matte finish.

* * * * *